(12) United States Patent
Vlodavsky et al.

(10) Patent No.: US 11,161,912 B2
(45) Date of Patent: Nov. 2, 2021

(54) HEPARANASE-NEUTRALIZING MONOCLONAL ANTIBODIES

(71) Applicants: Technion Research & Development Foundation Limited, Haifa (IL); Hadasit Medical Research Services and Development Ltd., Jerusalem (IL)

(72) Inventors: Israel Vlodavsky, Mevasseret Zion (IL); Marina Weissmann, Netanya (IL); Neta Ilan, Herzliya (IL); Gil Arvatz, Kfar Tavor (IL)

(73) Assignees: TECHNION RESEARCH & DEVELOPMENT FOUNDATION LIMITED, Haifa (IL); HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 168 days.

(21) Appl. No.: 15/767,355

(22) PCT Filed: Oct. 13, 2016

(86) PCT No.: PCT/IL2016/051118
§ 371 (c)(1),
(2) Date: Apr. 11, 2018

(87) PCT Pub. No.: WO2017/064716
PCT Pub. Date: Apr. 20, 2017

(65) Prior Publication Data
US 2019/0112391 A1 Apr. 18, 2019

Related U.S. Application Data

(60) Provisional application No. 62/240,549, filed on Oct. 13, 2015, provisional application No. 62/360,987, filed on Jul. 12, 2016.

(51) Int. Cl.
| | | |
|---|---|---|
| *C07K 16/40* | (2006.01) | |
| *C12N 9/24* | (2006.01) | |
| *A61P 31/00* | (2006.01) | |
| *A61P 35/04* | (2006.01) | |
| *A61P 35/00* | (2006.01) | |
| *A61K 39/395* | (2006.01) | |
| *A61K 45/06* | (2006.01) | |
| *C07K 16/30* | (2006.01) | |
| *A61K 39/00* | (2006.01) | |

(52) U.S. Cl.
CPC .......... *C07K 16/40* (2013.01); *A61K 39/3955* (2013.01); *A61K 45/06* (2013.01); *A61P 31/00* (2018.01); *A61P 35/00* (2018.01); *A61P 35/04* (2018.01); *C12N 9/2402* (2013.01); *C12Y 302/01166* (2013.01); *A61K 2039/505* (2013.01); *C07K 16/30* (2013.01); *C07K 2317/34* (2013.01); *C07K 2317/52* (2013.01); *C07K 2317/565* (2013.01); *C07K 2317/76* (2013.01)

(58) Field of Classification Search
CPC combination set(s) only.
See application file for complete search history.

(56) References Cited

U.S. PATENT DOCUMENTS

| | | | |
|---|---|---|---|
| 6,562,950 B2 | 5/2003 | Peretz et al. | |
| 7,772,187 B2 * | 8/2010 | Vlodavsky | ............. A61K 38/47 435/200 |
| 8,048,993 B2 | 11/2011 | Pecker et al. | |
| 2004/0170631 A1 | 9/2004 | Yacoby-Zeevi et al. | |
| 2005/0169907 A1 * | 8/2005 | Vlodavsky | ............. A61K 38/47 424/94.61 |
| 2005/0244929 A1 | 11/2005 | Carter | |

FOREIGN PATENT DOCUMENTS

| | | |
|---|---|---|
| WO | WO 2004/043989 A2 | 5/2004 |
| WO | WO 2005/071070 A2 | 8/2005 |
| WO | WO-2007/013050 | 2/2007 |
| WO | WO-2009/010957 | 1/2009 |
| WO | WO 2010/041060 A1 | 4/2010 |

OTHER PUBLICATIONS

Levy-Adam et al. "Identification and Characterization of Heparin/Heparan Sulfate Binding Domains of the Endoglycosidase Heparanase", The Journal of Biological Chemistry, vol. 280, No. 21, May 27, 2005, pp. 20457-20466.
International Search Report of Application No. PCT/IL2016/051118 dated Mar. 17, 2017.
Marina Weissmann et al.: "Heparanase-neutralizing antibodies attenuate lymphoma tumor growth and metastasis", Proceedings of the National Academy of Sciences of the United States of America, Jan. 19, 2016.
Lerner et al. " Heparanase powers a chronic inflammatory circuit that promotes colitis-associated tumorigenesis in mice ", J Clin Invest, 2011, vol. 121, No. 5, pp. 1709-1721.

(Continued)

*Primary Examiner* — Lei Yao
(74) *Attorney, Agent, or Firm* — Pearl Cohen Zedek Latzer Baratz LLP

(57) ABSTRACT

The present invention relates to heparanase-neutralizing monoclonal antibodies (m Abs), pharmaceutical composition comprising same, and use thereof for treating a disease or disorder associated with heparanase activity, including but not limited to cancer, inflammation, diabetes and related complications. The present invention further provides combined therapies comprising the heparanase-neutralizing m Ab and an anti-cancer treatment such as chemotherapy or radiation, for treating a proliferative disease in a subject.

15 Claims, 20 Drawing Sheets
Specification includes a Sequence Listing.

(56) References Cited

OTHER PUBLICATIONS

Vlodavsky, I. et al. " Expression of heparanase by platelets and circulating cells of the immune system: possible involvement in diapedesis and extravasation", Invasion & Metastasis, 1992, vol. 12, pp. 112-127.
Levidiotis et al." Increased expression of heparanase in puromycin aminonucleoside nephrosis ", Kidney Int., 2001, vol. 60, pp. 1287-1296.
Xiao et al."Heparanase expression in hepatocellular carcinoma and the cirrhotic liver", Hepatology Res., 2003, vol. 26, pp. 192-198.
Katz et al. " Involvement of Human Heparanase in the Pathogenesisof Diabetic Nephropathy ", Isr. Med. Assoc., 2002, vol. 4, pp. 996-1002.
Gil et al." Heparanase Is Essential for the Development of Diabetic Nephropathy in Mice ", Diabetes, 2012, vol. 61, pp. 208-216.
Ziolkowski et al. "Heparan sulfate and heparanase play key roles in mouse b cell survival and autoimmune diabetes", J Clin Invest 2012; 122:132-41.
Casu et al. "Non-Anticoagulant Heparins and Inhibition of Cancer", Pathophysiol Haemost Thromb, 2008, vol. 36, No. 3-4, pp. 195-203.
Naggi et al. "Modulation of the Heparanase-inhibiting Activity of Heparin through Selective Desulfation, Graded N-Acetylation, and Glycol Splitting*", J Biol Chem, 2005, vol. 280, No. 13, pp. 12103-13.
Ritchie et al. "SST0001, a Chemically Modified Heparin, Inhibits Myeloma Growth and Angiogenesis via Disruption of the Heparanase/Syndecan-1 Axis", J Biol CHEM, 2011.
Yang et al. "The syndecan-1 heparan sulfate proteoglycan is a viable target for myeloma therapy", Blood, 2007, vol. 110, No. 6, pp. 2041-2048.
Levidiotis V et al. "Heparanase inhibition reduces proteinuria in a model of accelerated anti-glomerular basement membrane antibody disease", Nephrology Carlton, 2005, vol. 10, No. 2, pp. 167-173.
Levy-Adam et al. "Identification and Characterizaion of Heparin/eparan Sulfate Binding Domains of the Endologycosidase Heparanase", Id J Biol Chem, 2005, vol. 280, No. 21, pp. 20457-66.
Zetser et al. "Processing and activation of latent heparanase occurs in lysosomes", J Cell Sci, 2004, vol. 117, No. 11, pp. 2249-2258.
Dredge et al. "PG545, a dual heparanase and angiogenesis inhibitor, induces potent anti-tumour and anti-metastatic efficacy in preclinical models", Br J Cancer, 2011, pp. 635-642.
He X et al. "Hypoxia Increases Heparanase-Dependent Tumor Cell Invasion, Which Can Be Inhibited by Antiheparanase Antibodies", Cancer Res, 2004, vol. 64, No. 11, pp. 3928-3933.
Myler Ha et al. "Novel Heparanase-lnhibiting Antibody Reduces Neointima Formation", J Biochem, 2006, vol. 139, No. 3, pp. 339-345.

* cited by examiner

SEQUENCE LISTING

```
<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Gly Phe Asp Phe Ser Arg Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Asn Pro Asp Ser Ser Thr Ile
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Arg Gly Tyr Glu Gly Asn Tyr Ala Met Asp Tyr
1               5                   10

<210> SEQ ID NO 4
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 4

Lys Ser Leu Leu His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Synthetic

<400> SEQUENCE: 5

Arg Met Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Met Gln His Leu Glu Tyr Pro Phe Thr
1               5

<210> SEQ ID NO 7
<211> LENGTH: 151
<212> TYPE: PRT
<213> ORGANISM: Artificial Sequence
<220> FEATURE:
<223> OTHER INFORMATION: Synthetic

<400> SEQUENCE: 7

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Arg Gly Tyr Glu Gly Asn Tyr Ala Met Asp Tyr Trp Gly Gln
            100                 105                 110

Gly Thr Ser Val Thr Val Ser Ser Glu Ser Gln Ser Phe Pro Asn Val
        115                 120                 125

Phe Pro Leu Val Ser Cys Glu Ser Pro Leu Ser Asp Lys Asn Leu Val
    130                 135                 140

Ala Met Gly Cys Leu Ala Arg
145                 150

<210> SEQ ID NO 8
```

<211> LENGTH: 141
<212> TYPE: PRT
<213> ORGANISM: Artificial Sequence
<220> FEATURE:
<223> OTHER INFORMATION: Synthetic

<400> SEQUENCE: 8

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu
    130                 135                 140
```

<210> SEQ ID NO 9
<211> LENGTH: 454
<212> TYPE: DNA
<213> ORGANISM: Artificial Sequence
<220> FEATURE:
<223> OTHER INFORMATION: Synthetic

<400> SEQUENCE: 9

```
gaggtgaagc ttctcgagtc tggaggtggc ctggtgcagc ctggaggatc cctgaaactc     60
tcctgtgcag cctcaggatt cgattttagt agatactgga tgagttgggt ccggcaggct    120
ccagggaaag ggctagaatg gattggagaa attaatccag atagcagtac gataaactat    180
acgccatctc taaaggataa attcatcatc tccagagaca acgccaaaaa tacgctgtac    240
ctgcaaatga gcaaagtgag atctgaggac acagcccttt attactgtgc aagacggggg    300
tacgagggta actatgctat ggactactgg ggtcaaggaa cctcagtcac cgtctcctca    360
gagagtcagt ccttccccaa tgtcttcccc ctcgtctcct gcgagagccc cctgtctgat    420
aagaatctgg tggccatggg ctgcctggcc cggg                                454
```

<210> SEQ ID NO 10
<211> LENGTH: 255
<212> TYPE: DNA
<213> ORGANISM: Artificial Sequence
<220> FEATURE:
<223> OTHER INFORMATION: Synthetic

<400> SEQUENCE: 10

```
gatattgtga tgactcaggc tgcaccctct gtacctgtca ctcctggtga gtcagtatcc     60
atctcctgca ggtctagtaa gagtctcctg catagtaatg caacacttac cttgtattgg    120
ttcctgcaga ggccaggcca gtctcctcag ctcctgatat atcggatgtc aaccttgcc     180 tcaggagtcc cagacaggtt cagtggcagt gggtcaggaa ctgctttcac actgagaatc    240
```
agtagagtgg aggct                                                                                      255

<210> SEQ ID NO 11
<211> LENGTH: 14
<212> TYPE: PRT
<213> ORGANISM: Homo sapiens

<400> SEQUENCE: 11

Lys Lys Phe Lys Asn Ser Thr Tyr Ser Arg Ser Ser Val Asp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ala Arg Arg Gly Tyr Glu Gly Asn Tyr Ala Met Asp Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Gly Phe Asp Phe Ser Arg Tyr Trp Met Ser
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Glu Ile Asn Pro Asp Ser Ser Thr Ile Asn Tyr Thr Pro Ser Leu Lys
1               5                   10                  15

Asp

<210> SEQ ID NO 15
<211> LENGTH: 16
<212> TYPE: PRT
<213> ORGANISM: Artificial Sequence
<220> FEATURE:
<223> OTHER INFORMATION: Synthetic

<400> SEQUENCE: 15

Arg Ser Ser Lys Ser Leu Leu His Ser Asn Gly Asn Thr Tyr Leu Tyr
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Arg Met Ser Asn Leu Ala Ser
1               5

```
<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gatattgtga tgactcaggc tgc                                              23

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gtagaagttg ttcaagaagc                                                  20

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gaggtgaagc ttctcgagtc tgg                                              23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
gggcaggaag tcccgggcca ggc                                              23
```

HEPARANASE-NEUTRALIZING MONOCLONAL ANTIBODIES

CROSS-REFERENCE TO RELATED APPLICATIONS

This application is a National Phase Application of PCT International Application No. PCT/IL2016/051118, International Filing Date Oct. 13, 2016, entitled "Heparanase-Neutralizing Monoclonal Antibodies", published on Apr. 20, 2017 as International Patent Application Publication No. WO 2017/064716 claiming the benefit of U.S. Patent Provisional Application No. 62/240,549, filed on Oct. 13, 2015 and U.S. Patent Provisional Application No. 62/360,987 filed on Jul. 12, 2016, both of which are incorporated by reference.

INCORPORATION OF SEQUENCE LISTING

A sequence listing containing the file named "P-78541-US-SEQ-03SEP18_ST25.txt" which is 3,870 characters (measured in MS-Windows®) and was created on Sep. 3, 2018, and comprises 20 sequences, and is incorporated herein by reference in its entirety.

FIELD OF THE INVENTION

The present invention relates to heparanase-neutralizing monoclonal antibodies, pharmaceutical composition comprising same, and use thereof for treating a disease or disorder associated with heparanase activity in a subject.

BACKGROUND OF THE INVENTION

Heparanase is an endo-β-D-glucuronidase capable of cleaving heparan sulfate (HS) side chains at a limited number of sites. Heparanase activity correlates with the metastatic potential of tumor-derived cells, attributed to enhanced cell dissemination as a consequence of HS cleavage and remodeling of the extracellular matrix (ECM) and basement membrane underlying epithelial and endothelial cells. Heparanase expression is induced in all major types of human cancer namely carcinomas, sarcomas and hematological malignancies. Increased heparanase levels are most often associated with reduced patients' survival post operation, increased tumor metastasis and higher microvessel density. In addition, heparanase up-regulation was associated with tumor larger in size. Likewise, heparanase overexpression enhanced, while local delivery of anti-heparanase siRNA inhibited the growth of tumor xenografts. These results imply that heparanase function is not limited to tumor metastasis but is engaged in progression of the primary lesion, thus critically supporting the intimate involvement of heparanase in tumor progression and encouraging the development of heparanase inhibitors as anti-cancer therapeutics.

Heparanase has also been shown to facilitate cell invasion associated with autoimmunity, inflammation (Lerner et al. J Clin Invest 2011; 121(5):1709-21) and angiogenesis (Vlodaysky et al., Invasion & Metastasis 1992; 12, 112-127). In addition, increased heparanase expression has been noted in kidney (Levidiotis et al., Kidney Int. 60, 1287-1296, 2001), liver (Xiao et al., Hepatology Res. 26, 192-198, 2003) and diabetic (Katz et al., Isr. Med. Assoc. 4, 996-1002, 2002; Gil et al. Diabetes 2012; 61: 208-16, and Ziolkowski et al. 2012; 122:132-41) disorders.

The finding that heparanase is involved in a wide variety of pathological processes has led to development of therapeutic compounds to inhibit this enzyme including, PI-88, a phosphomannopentaose sulfate, and SST0001, a modified heparin that is 100% N-acetylated and 25% glycol split. SST0001 is endowed with little or no anti-coagulant activity, exerts highly diminished undesired release and activation of ECM-bound pro-angiogenic factors (i.e., bFGF) (Casu et al. Pathophysiol Haemost Thromb 2008; 36(3-4):195-203; Naggi et al. J Biol Chem 2005; 280(13):12103-13), and has proven efficacious in several tumor model systems (Ritchie et al, 2011, ibid; Yang et al. Blood 2007; 110(6):2041-8.), yet it may still exhibit heparanase enzymatic activity-unrelated properties (Levidiotis et al. Nephrology (Carlton) 2005; 10(2):167-73).

Three potential heparin-binding domains of heparanase were identified by the present inventors and co-workers (Levy-Adam et al. Id J Biol Chem 2005; 280(21):20457-66). Particular attention was given to the Lys158-Asp171 domain since a peptide corresponding to this sequence (termed KKDC) physically interacts with heparin and HS with high affinity and inhibits heparanase enzymatic activity. Furthermore, deletion construct lacking this domain exhibits no enzymatic activity and polyclonal antibody (Ab #733) directed to this region inhibits heparanase activity (Zetser et al. J Cell Sci 2004; 117(11):2249-58).

Attempts to inhibit heparanase enzymatic activity were initiated already at the early days of heparanase research, in parallel with the emerging clinical relevance of this activity. More recently, a variety of inhibitory molecules have been developed, including peptides, small molecules, modified non-anticoagulant species of heparin, as well as several other polyanionic molecules such as laminaran sulfate, suramin, PI-88, and PG545 (Dredge et al. Br J Cancer 2011, 635-42). Similarly, anti-heparanase polyclonal antibodies were developed and demonstrated to neutralize heparanase enzymatic activity and to inhibit cell invasion (He X et al. Cancer Res 2004; 64(11):3928-33), proteinuria (Levidiotis V, et al. Nephrology (Carlton) 2005; 10(2):167-73) and neointima formation (Myler H A, et al. J Biochem 2006; 139(3):339-45). Neutralizing anti-heparanase monoclonal antibodies, however, have not been so far reported.

U.S. Pat. No. 7,772,187 by some of the inventors of the present invention and a coworker relates to an amino acid sequence derived from the N' terminus region of the 50 Kd subunit of heparanase, and particularly to the sequence of Lys158-Asn171 of human heparanase. The '187 patent further discloses a polyclonal antibody directed to the sequence and compositions and uses thereof as heparanase inhibitor.

U.S. Pat. No. 6,562,950 by an inventor of the present invention and coworkers provides a monoclonal antibody elicited by a heparanase protein or an immunogenic portion thereof, which specifically inhibits heparanase activity. The '950 patent disclosed two monoclonal antibodies HP-130 and H-239. Notably, the HP-239 which recognized an internal epitope localized to amino acids 130-230 caused no inhibition of heparanase activity whereas HP-130 formed against the C-terminus of heparanase almost completely inhibited its activity.

U.S. Pat. No. 8,048,993 by an inventor of the present invention and coworkers provides an antibody that specifically binds an epitope of a heparanase protein provided that phenylalanine replaces tyrosine at position 246 of the heparanase protein.

None of the background art teaches or suggests specific monoclonal antibodies, which bind the Lys158-Asp171 domain of heparanase and neutralizes heparanase activity. Thus, there is an unmet need to provide highly specific heparanase-neutralizing monoclonal antibodies, which can be used prevent and treat medical conditions associated with heparanase activity.

SUMMARY OF THE INVENTION

The present invention provides heparanase-neutralizing monoclonal antibodies (mAbs), pharmaceutical composition comprising same, and use thereof for treating a disease or disorder associated with heparanase activity, including but not limited to malignant proliferative diseases.

The present invention is based in part on the development of a neutralizing mAb directed against heparanase N' terminus region, particularly against the Lys158-Asp171 domain. The mAb recognizes the heparan sulfate (HS) binding domain of heparanase, neutralizing its function and ultimately resulting in a marked inhibition of cellular invasion and metastasis.

Thus, in some embodiments, the present invention provides specific mAbs directed against the Lys158-Asp171 domain of human heparanase, enabling the targeting of heparanase enzymatic activity. The mAbs of the invention are thus useful in attenuating and treating diseases and disorders associated with heparanase enzymatic activity, as a single agent or in combination with at least one additional conventional therapy including but not limited to chemotherapy or radiation.

According to a first aspect, the invention provides a neutralizing monoclonal antibody (mAb), or an antibody fragment comprising at least an antigen-binding portion thereof, directed against the Lys158-Asp171 domain of human heparanase. According to another embodiment, said Lys158-Asp171 domain of human heparanase has the amino acid sequence as set forth in SEQ ID NO: 11 (KKFKN-STYSRSSVD). According to another embodiment the mAb or antibody fragment thereof has a heparanase neutralizing effect.

According to an embodiment of the invention, there is provided an antibody or an antibody fragment thereof comprising at least one heavy-chain CDR selected from the group consisting of: SEQ ID NO: 1 or a functional variant thereof, SEQ ID NO: 2 or a functional variant thereof and SEQ ID NO: 3 or a functional variant thereof, and at least one light-chain CDR selected from the group consisting of: SEQ ID NO: 4 or a functional variant thereof, SEQ ID NO: 5 or a functional variant thereof and SEQ ID NO: 6 or a functional variant thereof, wherein the functional variant for each of the sequences 1, 2, 3, 4, 5 or 6 has at least 70, 80, 85, 90, 91, 92, 93, 94, 95, 96, 97, 98 or 99% sequence similarity or identity with SEQ ID NO:1, SEQ ID NO:2, SEQ ID NO:3, SEQ ID NO:4, SEQ ID NO:5, SEQ ID NO:6, respectively.

According to another embodiment, the mAb comprises a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO:6, and analogs and derivatives thereof.

According to another embodiment, the mAb comprises a heavy chain variable domain sequence having an amino acid sequence set forth in SEQ ID NO: 7, or an analog or derivative thereof having at least 70, 80, 85, 90, 91, 92, 93, 94, 95, 96, 97, 98 or 99% sequence similarity or identity with the heavy chain sequence set forth in SEQ ID NO: 7.

According to another embodiment, the mAb comprises a light chain variable domain sequence having an amino acid sequence set forth in SEQ ID NO: 8, or an analog or derivative thereof having at least 70, 80, 85, 90, 91, 92, 93, 94, 95, 96, 97, 98 or 99% sequence similarity or identity with the light chain sequence set forth in SEQ ID NO: 8.

According to another embodiment, the mAb comprises a heavy chain variable domain having a sequence set forth in SEQ ID NO: 7 and a light chain variable domain having a sequence set forth in SEQ ID NO: 8.

According to another embodiment, the mAb comprises an analog or derivative of SEQ ID NO:7 or SEQ ID NO:8 which has at least 70, 80, 85, 90, 91, 92, 93, 94, 95, 96, 97, 98 or 99% sequence similarity or identity with the light chain sequence set forth in SEQ ID NO: 7 or SEQ ID NO: 8.

According to another embodiment, the antibody fragment is selected from the group consisting of: Fab, Fab', F(ab')$_2$, Fd, Fd', Fv, dAb, isolated CDR region, scFv-Fc fragment, single chain antibody, a nanobody, a minibody diabody, triabody, or an tetrabody, or a linear antibody.

According to another embodiment, the antibody, antibody fragment or the mAb is attached to a functional moiety.

The functional moiety is in some embodiments a marker, detectable tag, cytotoxic molecule or therapeutic agent.

According to another embodiment, the antibody, antibody fragment or the mAb of the invention is a monoclonal antibody.

According to another embodiment, the mAb is of an immunoglobulin class including IgG, IgM, IgE, IgA, and any subclass thereof.

According to another embodiment, the immunoglobulin is selected from the group consisting of IgA1, IgA2, IgD, IgE, IgG1, IgG2, IgG3 and IgG4.

According to another embodiment, the heavy chain variable domain of the antibody or the antibody fragment or the mAb of the invention is joined to the constant heavy region of a human IgG antibody subtype.

According to another embodiment, there is provided an isolated polynucleotide sequence encoding a antibody, mAb or the antibody fragment thereof according to the embodiments described herein.

According to another embodiment, the isolated nucleotide encoding a heavy chain variable region comprises the nucleotide sequence as set forth in SEQ ID NO: 9.

According to another embodiment, the isolated nucleotide encoding a light chain variable region comprises the nucleotide sequence as set forth in SEQ ID NO: 10.

According to another embodiment, there is provided a vector that comprises the isolated nucleotide encoding the antibody of the invention and a host cell that comprises the vector.

According to another embodiment, there is provided a pharmaceutical composition comprising the antibody, antibody fragment or the mAb as described herein, or an antibody fragment thereof, and a pharmaceutical acceptable carrier.

According to some embodiments, the antibody, antibody fragment or the mAb of the invention or an antibody fragment thereof, or the pharmaceutical composition including them are used in a method for treating lymphoma in a subject in need thereof, comprising administering to the subject a therapeutically effective amount of the mAb or an antibody fragment thereof, or the pharmaceutical composition comprising mAb or an antibody fragment thereof thereby treating the lymphoma in said subject.

According to some embodiments, the lymphoma is a B-cell lymphoma.

According to some embodiments, the B-cell lymphoma is selected from the group consisting of Burkitt lymphoma, Hodgkin's lymphoma, non-Hodgkin's lymphoma, follicular lymphoma, small lymphocytic lymphoma, diffuse B-cell lymphoma, mantle cell lymphoma, marginal zone lymphoma.

According to some embodiments, the antibody of the invention or the antibody fragment thereof or the mAb, or the pharmaceutical composition including them are used in a method for treating multiple myeloma in a subject in need thereof, comprising administering to the subject a therapeutically effective amount of the antibody of the invention or the antibody fragment thereof, or the mAb, or a pharmaceutical composition comprising a therapeutically effective amount of the antibody of the invention or the antibody fragment thereof or the mAb, thereby treating the multiple myeloma in the subject.

According to some embodiments, the antibody or the mAb of the invention or an antibody fragment thereof, or the pharmaceutical composition comprising thereof are administered in combination with an anti-cancer treatment.

The anti-cancer treatment according to some embodiments is selected from the group consisting of chemotherapy, surgery, radiotherapy, hyperthermia, immunotherapy, hormone therapy, biologic therapy.

According to another aspect there is provided a method for neutralizing heparanase activity comprising contacting a cell with the mAb of the invention or an antibody fragment thereof.

Further embodiments and the full scope of applicability of the present invention will become apparent from the detailed description given hereinafter.

DETAILED DESCRIPTION OF THE INVENTION

Figure 1A:
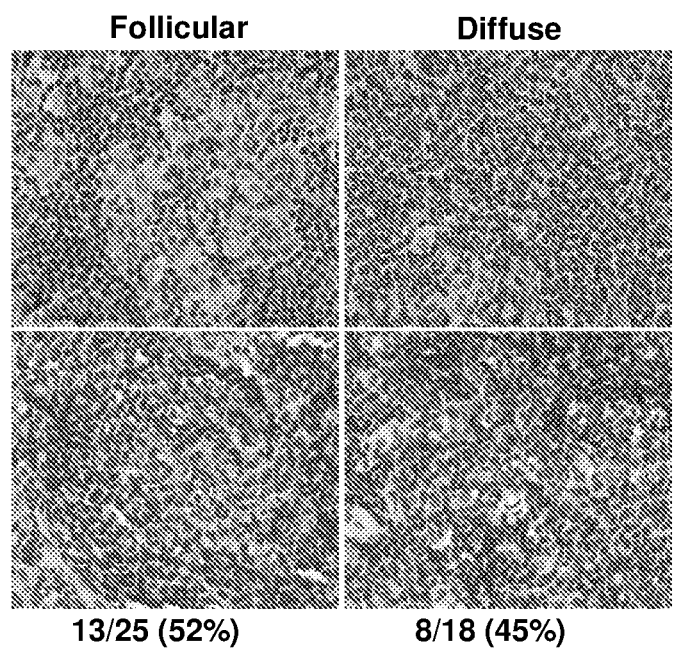
FIG. 1A show specimens of human follicular (left panel) and diffuse (right panel) B-cell lymphomas immuno-stained with anti-heparanase antibody.

The present invention relates to heparanase-neutralizing monoclonal antibodies (mAbs), pharmaceutical composition comprising same, and use thereof for treating a disease or disorder associated with heparanase activity, including but not limited to malignant diseases.

The present invention is based, in part, on the development of mAb which neutralizes heparanase enzymatic activity. As exemplified herein, the mAb of the invention targets the heparin/HS-binding domain, residing at amino acid residues Lys158-Asn171 of human heparanase, and interferes with heparanase activity. The mAb substantially decreased uptake of latent and active heparanase, a HS-dependent cellular mechanism thought to limit extracellular retention of the active enzyme, thereby preventing adverse outcomes. Decreased intracellular content of the 50 kDa processed heparanase in cells incubated with the mAb indicates that the antibody not only neutralizes the enzyme extracellularly but also affects heparanase levels and activity inside the cell. Utilizing human lymphoma and myeloma cells we show that the heparanase neutralizing monoclonal antibodies profoundly inhibit tumor load in the mouse bones, associating with reduced cell proliferation and angiogenesis (Weissmann et al, 2016, Proc Natl Acad Sci USA 113:704-709).

The antibodies of the present invention, such as mAb 9E8, exert high specificity, enabling solely the targeting of heparanase enzymatic activity. Thus, the antibodies of the invention are useful in attenuating and treating diseases and disorders associated with heparanase activity, including but not limited to, tumor progression, inflammation, type 1 diabetes and diabetic nephropathy, as single agent or in combination with at least one additional therapy including but not limited to chemotherapy or radiation.

Nucleotide and amino acid sequences of mAb 9E8 are shown in Table 1. Mouse IgM (Sigma) was used as control. Anti-heparanase 1453 polyclonal antibody was raised against the entire 65 kDa latent heparanase protein (Zetser et al. J Cell Sci 2004; 117(11):2249-58).

TABLE 1

Nucleotide and amino acid sequences of mAb 9E8

| Variable Chain | | Sequence | SEQ ID NO: |
|---|---|---|---|
| Variable Heavy Chain | Amino acid sequence | EVKLLESGGGLVQPGGSLKLSCAASGFDFSRY WMSWVRQAPGKGLEWIGEINPDSSTINYTPSL KDKFIISRDNAKNTLYLQMSKVRSEDTALYYC ARRGYEGNYAMDYWGQGTSVTVSSESQSFPNV FPLVSCESPLSDKNLVAMGCLAR | 7 |
| | Nucleic acid sequence | GAGGTGAAGCTTCTCGAGTCTGGAGGTGGCCT GGTGCAGCCTGGAGGATCCCTGAAACTCTCCT GTGCAGCCTCAGGATTCGATTTTAGTAGATAC TGGATGAGTTGGGTCCGGCAGGCTCCAGGGAA AGGGCTAGAATGGATTGGAGAAATTAATCCAG ATAGCAGTACGATAAACTATACGCCATCTCTA AAGGATAAATTCATCATCTCCAGAGACAACGC CAAAAATACGCTGTACCTGCAAATGAGCAAAG TGAGATCTGAGGACACAGCCCTTTATTACTGT GCAAGACGGGGGTACGAGGGTAACTATGCTAT GGACTACTGGGGTCAAGGAACCTCAGTCACCG TCTCCTCAGAGAGTCAGTCCTTCCCAAATGTC TTCCCCCTCGTCTCCTGCGAGAGCCCCTGTC TGATAAGAATCTGGTGGCCATGGGCTGCCTGG CCCGGG | 9 |
| | CDR-H1 | GFDFSRY | 1 |
| | CDR-H1 | GFDFSRYWMS | 13 |
| | CDR-H2 | INPDSSTI | 2 |
| | CDR-H2 | EINPDSSTINYTPSLKD | 14 |
| | CDR-H3 | RGYEGNYAMDY | 3 |
| | CDR-H3 | ARRGYEGNYAMDY | 12 |

TABLE 1-continued

Nucleotide and amino acid sequences of mAb 9E8

| Variable Chain | | Sequence | SEQ ID NO: |
|---|---|---|---|
| Variable Light Chain | Amino acid sequence | DIVMTQAAPSVPVTPGESVSISCRSSKSLLHS NGNTYLYWFLQRPGQSPQLLIYRMSNLASGVP DRFSGSGSGTAFTLRISRVEAEDVGVYYCMQH LEYPFTFGSGTKLEIKRADAAPTVSIFPPSSE QLTSGGASVVCFL | 8 |
| | CDR-L1 | KSLLHSNGNTY | 4 |
| | CDR-L1 | RSSKSLLHSNGNTYLY | 15 |
| | CDR-L2 | RMS | 5 |
| | CDR-L2 | RMSNLAS | 16 |
| | CDR-L3 | MQHLEYPFT | 6 |
| | Nucleic acid sequence | GATATTGTGATGACTCAGGCTGCACCCTCTGT ACCTGTCACTCCTGGTGAGTCAGTATCCATCT CCTGCAGGTCTAGTAAGAGTCTCCTGCATAGT AATGGCAACACTTACTTGTATTGGTTCCTGCA GAGGCCAGGCCAGTCTCCTCAGCTCCTGATAT ATCGGATGTCCAACCTTGCCTCAGGAGTCCCA GACAGGTTCAGTGGCAGTGGGTCAGGAACTGC TTTCACACTGAGAATCAGTAGAGTGGAGGCTG AGGATGTGGGTGTTTATTACTGTATGCAACAT CTAGAATATCCATTCACGTTCGGCTCGGGGAC AAAGTTGGAAATAAAACGGGCTGATGCTGCAC CAACTGTATCCATCTTCCCACCATCCAGTGAG CAGTTAACATCTGGAGGTGCCTCAGTCGTGTG CTTCTTGAA | 10 |

According to another embodiment a mAb or antibody fragment thereof is provided comprising at least one heavy-chain CDR selected from the group consisting of:

(i) a heavy-chain CDR1 (CDR-H1) comprising a sequence set forth in
SEQ ID NO: 1
(GFDFSRY);

(ii) a heavy-chain CDR2 (CDR-H2) comprising a sequence set forth in
SEQ ID NO: 2
(INPDSSTI);
and (iii) a heavy-chain CDR3 (CDR-H3) comprising a sequence set forth in
SEQ ID NO: 3
(RGYEGNYAMDY).

According to another embodiment the at least one heavy-chain CDR is selected from the group consisting of: CDR-H1 (SEQ ID NO: 1; GFDFSRY), CDR-H2 (SEQ ID NO: 2; INPDSSTI) and CDR-H3 (SEQ ID NO: 12 (ARRGYEGNYAMDY). According to yet another embodiment the at least one heavy-chain CDR is selected from the group consisting of: CDR-H1 (SEQ ID NO: 13; GFDFSRYWMS), CDR-H2 (SEQ ID NO: 14; EINPDSSTINYTPSLKD) and CDR-H3 (SEQ ID NO: 3; RGYEGNYAMDY).

According to another embodiment a mAb or antibody fragment thereof is provided comprising at least one light-chain CDR selected from the group consisting of:

(i) a light-chain CDR1 (CDR-L1) comprising a
sequence set forth in
                                         SEQ ID NO: 4
(KSLLHSNGNTY);

(ii) a light-chain CDR2 (CDR-L2) comprising a
sequence set forth in
                                         SEQ ID NO: 5
(RMS);
and (iii) (ii) a light-chain CDR3 (CDR-L3) comprising
a sequence set forth in
                                         SEQ ID NO: 6
(MQHLEYPFT).

According to yet another embodiment the at least one light-chain CDR is selected from the group consisting of: CDR-L1 (SEQ ID NO: 15; RSSKSLLHSNGNTYLY), CDR-L2 (SEQ ID NO: 16; RMSNLAS) and CDR-L3 (SEQ ID NO: 6; MQHLEYPFT).

According to some embodiments, the present invention provides a mAb or antibody fragment thereof comprising a heavy chain variable domain sequence having an amino acid sequence set forth in SEQ ID NO: 7:
EVKLLESGGGLVQPGGSLKLS-CAASGFDFSRYWMSWVRQAPGKGLEWIG EINPDSSTINYTPSLKDKFIISRDNAKNT-LYLQMSKVRSEDTALYYCARRGYEGN YAMDYWGQGTSVTVSS-ESQSFPNVFPLVSCESPLSDKNLVAMGCLAR, or an analog or derivative thereof having at least 70% sequence identity with the heavy chain sequence. In some embodiments, the analog or derivative has at least 75%, at least 80%, at least 85%, at least 90% or at least 95% sequence identity with SEQ ID NO: 7.

According to another embodiment, the present invention provides a mAb or antibody fragment thereof comprising a light chain variable domain sequence having an amino acid sequence set forth in SEQ ID NO: 8:
DIVMTQAAPSVPVTPGESVSISCRSSKSLLHSNGN-TYLYWFLQRPGQSPQL LIYRMSN-LASGVPDRFSGSGSGTAFTLRISRVEAE-DVGVYYCMQHLEYPFTFGS GTKLEIKRADAAPTVSIFPPSSEQLTSGGASVVCFL, or an analog or derivative thereof having at least 70% sequence identity with the light chain sequence. In some embodiments, the analog or derivative has at least 75%, at least 80%, at least 85%, at least 90% or at least 95% sequence identity with SEQ ID NO: 8.

According to a specific embodiment the antibody or fragment thereof comprises a heavy chain variable domain having a sequence set forth in SEQ ID NO: 7 and a light chain variable domain having a sequence set forth in SEQ ID NO: 8.

Analogs and derivatives of the monoclonal antibody or fragment thereof, having at least 70% sequence identity with the antigen-binding portion of the reference sequence are also within the scope of the present invention. According to some embodiments, analogs and derivatives of the monoclonal antibody or fragment thereof having at least 80%, at least 85%, at least 90% or at least 95% sequence identity with the antigen-binding portion of the reference sequence are provided.

The term "having at least X percent identity" refers to the percent of amino acid residues that are identical in the two compared sequences when the sequences are optimally aligned. Thus, 70% amino acid sequence identity means that 70% of the amino acids in two or more optimally aligned polypeptide sequences are identical.

A monoclonal antibody according to the present invention may contain a constant region from any mammalian species, including but not limited to mouse, rat and human. A monoclonal antibody according to the present invention includes a chimeric antibody, a humanized antibody, a fully human antibody, a xenogeneic antibody, and an antibody fragment comprising at least the antigen-binding portion of an antibody.

The present invention encompasses monoclonal antibodies isolated from hybridoma cells or other biological systems, as well as monoclonal antibodies produced recombinantly or synthetically. The hybridomas may be prepared by any of the methods known in the art (for example, Kohler, G. and Milstein, C., *Nature,* 256:495-497, (1975)). The supernatant of the hybridoma cell lines are typically screened for antibody binding activity by any one of the methods known in the art such as by enzyme linked immuno sorbent assay (ELISA) or radio immuno assay (RIA). The supernatants may be screened for production of mAbs which bind the KKDC peptide.

DNA sequences which encode any of the amino acid sequences of the heavy chain or light chain of the above mAbs are also encompassed within the scope of the invention. As will no doubt be clear to any man skilled in the art, due to the degenerative nature of the genetic code a plurality of nucleic acid sequences may code for the mAb of the invention beyond those shown in SEQ ID NO 9 or 10. The invention also provides expression vectors such as plasmids having said DNA sequences as well as host cells containing one or more of these expression vectors.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab, include regions where the polypeptide sequence varies. The term F(ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired biological activity.

The antibody according to the present invention is a molecule comprising at least the antigen-binding portion of an antibody. In specific embodiments, the antibody or antibodies according to the invention are monoclonal antibodies (mAbs), as well as proteolytic fragments thereof such as the Fab or F(ab')$_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies. Single chain antibodies also fall within the scope of the present invention.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CHI domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et at, Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

A "neutralizing antibody" as used herein refers to a molecule having an antigen-binding site to a specific ligand target (e.g. heparanase) capable of reducing or inhibiting (blocking) activity or signaling through the target, as determined by in vivo or in vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs of the present invention may be of any immunoglobulin class including IgG, IgM, IgE, IgA, and any subclass thereof. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol., 1992 2, 593-596.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 1996 14, 309-314; Sheets et al. PNAS (USA), 1998, 95, 6157-6162); Hoogenboom and Winter, J. Mol. Biol., 1991, 227, 381; Marks et al., J. Mol. Biol., 1991, 222, 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et at, J. Immunol., 147 (1):86-95 (1991); and U.S. Pat. No. 5,750,373.

By the term "single chain variable fragment (scFv)" is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked VH-VL or single chain Fv (scFv)). Both VH and VL may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the VH and VL chains are known, may be accomplished in accordance with the methods described, for example, in U.S. Pat. Nos. 4,946,778, 5,091,513 and 5,096,815, the entire contents of each of which are incorporated herein by reference.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific mini-antibodies (see Muller et al., 1998) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

For preparation of monoclonal antibodies, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

Compositions, Administration and Dosages

For use in the methods of the invention, the monoclonal antibody may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous intramuscular, subcutaneous, or intraperitoneal administration and conveniently comprise sterile aqueous solutions of the antibody, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with carriers, such as lactose, sucrose, starch, talc magnesium stearate, crystalline cellulose, methyl cellulose, carboxymethyl cellulose, glycerin, sodium alginate or gum arabic.

The mAb of the invention may be administered parenterally, generally by intravenous infusion. Administration may also be by intraperitoneal, oral, subcutaneous, or intramuscular routes. Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric and humanized antibodies are expected to have circulatory half-lives of up to four and up to 14-21 days, respectively. In some cases it may be advantageous to administer a large loading dose followed by periodic (e.g., weekly) maintenance doses over the treatment period. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained.

Typically, the effective dose will be determined by the condition of the subject, as well as the body weight or surface area of the subject to be treated. The size of the dose and the dosing regimen also will be determined by the existence, nature, and extent of any adverse side effects that accompany the administration of the mAb or a combination of an additional therapeutic agent in a particular subject. In determining the effective amount of the therapeutic composition to be administered, the physician needs to evaluate inter alia circulating plasma levels, toxicity, and progression of the disease.

Chemotherapy

According to yet another embodiment there is provided combined cancer therapy comprising the administration of the mAb of the invention and at least one chemotherapeutic agent.

Chemotherapy drugs are divided into several groups based on their effect on cancer cells, the cellular activities or processes the drug interferes with, or the specific phases of the cell cycle the drug affects. Accordingly, chemotherapy drugs fall in one of the following categories: alkylating agents, nitrosoureas, antimetabolites, anthracyclines, topoisomerase I and II inhibitors, mitotic inhibitors, inter alia platinum based drugs, steroids and anti-angiogenic agents.

Antimetabolites, also termed "nucleoside analogs", replace natural substances as building blocks in DNA molecules, thereby altering the function of enzymes required for cell metabolism and protein synthesis. In the event that they mimic nutrients required for cell growth, the cells eventually undergo lysis. If a nucleoside is replaced with a nonfunctional nucleoside analog, the latter is incorporated into DNA and RNA, finally inducing cell cycle arrest and apoptosis by inhibiting the cell's ability to synthesize DNA. Antimetabolites are cell-cycle specific and are most effective during the S-phase of cell division as they primarily act upon cells undergoing synthesis of new DNA for formation of new cells. The toxicities associated with these drugs are seen in cells that are growing and dividing quickly. Examples of antimetabolites include purine antagonists, pyrimidine antagonists, and folate antagonists. These agents damage cells during the S phase and are commonly used to treat leukemias, tumors of the breast, ovary, and the gastrointestinal tract, as well as other cancers. Specific examples of antimetabolites include 5-fluorouracil (also known as 5FU), capecitabine, 6-mercaptopurine, methotrexate, gemcitabine, cytarabine, fludarabine and pemetrexed.

Platinum-based chemotherapeutic drugs crosslink DNA in several different ways, interfering with cell division by mitosis. The damaged DNA elicits DNA repair mechanisms, which in turn activate apoptosis when repair proves impossible. Most notable among the DNA changes are the 1,2-intrastrand cross-links with purine bases. These include 1,2-intrastrand d(GpG) adducts which form nearly 90% of the adducts and the less common 1,2-intrastrand d(ApG) adducts. 1,3-intrastrand d(GpXpG) adducts occur but are readily excised by the nucleotide excision repair (NER). Other adducts include inter-strand crosslinks and nonfunctional adducts that have been postulated to contribute to the activity of platinum-based drugs. Interaction with cellular proteins, particularly HMG domain proteins, has also been advanced as a mechanism of interfering with mitosis, although this is probably not its primary method of action. Platinum-based chemotherapeutic drugs include cisplatin (also known as cisplatinum or cis-diamminedichloridoplatinum II (CDDP), carboplatin and oxaliplatin. Cisplatin is frequently designated as an alkylating agent, though it has no alkyl group and cannot carry out alkylating reactions. It is correctly classified as alkylating-like. Platinum-based chemotherapeutic drugs are used to treat various types of cancers, including sarcomas, some carcinomas (e.g. small cell lung cancer, and ovarian cancer), lymphomas and germ cell tumors.

Mitotic inhibitors interfere with cell division. The most known chemotherapeutic agent in this category is paclitaxel (also known as Taxol®, "plant alkaloid", "taxane" and an "antimicrotubule agent"). Together with docetaxel, it forms the drug category of the taxanes. However, other mitotic inhibitors are known, including, but not limited to etoposide, vinblastine and vincristine. Paclitaxel acts by interfering with normal microtubule growth during cell division by arrests their function; it hyper-stabilizes their structure. This destroys the cell's ability to use its cytoskeleton in a flexible manner. Specifically, paclitaxel binds to the subunit of tubulin, the "building block" of microtubules, and the binding of paclitaxel locks these building blocks in place. The resulting microtubule/paclitaxel complex does not have the ability to disassemble. This adversely affects cell function because the shortening and lengthening of microtubules (termed dynamic instability) is necessary for their function as a mechanism to transport other cellular components. For example, during mitosis, microtubules position the chromosomes all through their replication and subsequent separation into the two daughter-cell nuclei. Furthermore, paclitaxel induces programmed cell death (apoptosis) in cancer cells by binding to the apoptosis stopping protein Bcl-2 (B-cell leukemia 2) and thus arresting its function.

Another group of DNA-interacting drugs widely used in anti-cancer chemotherapy is the group of anthracycline antibiotics which includes, inter alia, daunorubicin, doxorubicin (also known as Adriamycin® and doxorubicin hydrochloride), respinomycin D and idarubicin. These drugs interact with DNA by intercalation and inhibition of macromolecular biosynthesis thereby inhibiting the progression of the enzyme topoisomerase II, which unwinds DNA for transcription. They stabilize the topoisomerase II complex after it has broken the DNA chain for replication, preventing the DNA double helix from being resealed and thereby stopping the process of replication. It is commonly used in the treatment of a wide range of cancers.

Alkylating antineoplastic agents directly attack DNA. They attach an alkyl group to DNA, cross-linking guanine nucleobases in DNA double-helix strands. This makes the strands unable to uncoil and separate. As this is necessary in DNA replication, the cells can no longer divide. These drugs act nonspecifically. Cyclophosphamide is an alkylating agent, however, it is a highly potent immunosuppressive substance.

Topoisomerase I and II inhibitors interfere with the enzymatic activity of topoisomerase I and 2, respectively, eventually leading to inhibition of both DNA replication and transcription. Examples of topoisomerase I inhibitors include topotecan and irinotecan. Irinotecan, is a prodrug converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death. Because ongoing DNA synthesis is necessary for irinotecan to exert its cytotoxic effects, it is also classified as an S-phase-specific agent. Examples of topoisomerase II inhibitors include etoposide and teniposide.

Anti-angiogenic agents interfere with the generation of new blood vessels, eventually leading to the "starvation" of tumors. Non-limiting examples of anti-angiogenic agents include the monoclonal antibody bevacizumab, dopamine and tetrathiomolybdate.

Vascular endothelial growth factor (VEGF) is a 32-42 kDa dimeric glycoprotein which mediates vasodilatation, increased vascular permeability and endothelial cell mitogenesis. Differential exon splicing of the VEGF gene results in three main mRNA species which code for three secreted isoforms (subscripts denote numbers of amino acids): VEGF189, VEGF165, and VEGF121. A number of minor splice variants have also been described (VEGF206, VEGF183, VEGF145 and VEGF148). Variants of VEGF polypeptides and their use in cancer therapy is disclosed for example, in WO/2003/012105.

According to various embodiments, the at least one chemotherapeutic agent is selected from the group consisting of: antimetabolites, platinum-based drugs, mitotic inhibitors, anthracycline antibiotics, topoisomerase inhibitors, anti-angiogenic agents and combinations thereof.

According to some embodiments, the at least one chemotherapeutic agent is an antimetabolite, including purine antagonists, pyrimidine antagonists and folate antagonists. According to some embodiments, the antimetabolite is a pyrimidine antagonist. According to some embodiments, the antimetabolite is selected from the group consisting of: methotrexate, pemetrexed, cladribine, clofarabine, fludarabine, 6-mercaptopurine, nelarabine, pentostatin, capecitabine, cytarabine, 5-fluorouracil, uracil mustard, uracil, gemcitabine, hydroxyurea and fludarabine.

According to some embodiments, the at least one chemotherapeutic agent is a platinum-based drug including but not limited to cisplatin, carboplatin and oxaliplatin.

According to yet other embodiments, the at least one chemotherapeutic agent is a mitotic inhibitor including but not limited to paclitaxel, docetaxel, etoposide, vinblastine, vincristine and vinorelbine.

According to yet other embodiments, the at least one chemotherapeutic agent is an anthracycline antibiotic including but not limited to daunorubicin, respinomycin D and idarubicin.

According to some embodiments, the at least one chemotherapeutic agent is an anti-angiogenic agent including but not limited to bevacizumab, dopamine, tetrathiomolybdate, and antiangiogenic drugs directed against VEGF and VEGF variants.

According to some embodiments, the at least one chemotherapeutic agent is a topoisomerase inhibitor including but not limited to daunorubicin, doxorubicin, epirubicin, irinotecan, topotecan, etoposide and mitoxantrone.

According to some embodiments, the at least one chemotherapeutic agent is an alkylating agent including but not limited to carmustine, lomustine, bendamustine, dacarbazine and procarbazine.

Brachytherapy

According to yet another embodiment there is provided combined cancer therapy comprising the mAb of the invention and radiation treatments. Radiation is administered in accordance with well known standard techniques using standard equipment manufactured for this purpose, such as AECL Theratron and Varian Clinac.

The distance between the source of the external radiation and the point of entry into the patient may be any distance that represents an acceptable balance between killing target cells and minimizing side effects. Typically, the source of the external radiation is between 70 and 100 cm from the point of entry into the patient.

The source of radiation that may be used in combination with the mAb of the invention and the chemotherapeutic agent(s) can be either external or internal to the patient being treated. When the source is external to the patient, the therapy is known as external beam radiation therapy (EBRT). When the source of radiation is internal to the patient, the treatment is called brachytherapy (BT).

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the invention is not limited to any particular dose. The dose will be determined by the treating physician in accordance with the particular factors in a given situation, including the factors mentioned above.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

In another embodiment the anti-cancer treatment is a heparanase inhibitor, including but not limited to, glycol-split heparin compounds (e.g., SST0001).

In various embodiments of the combination methods of the invention, the mAb and the at least one drug or treatment (e.g., chemotherapy, radiation therapy) may be administered according to any of a number of treatment schedules, also referred to "dosing schedules" and "administration regimens", referring to the frequency of administration and order of administration of each active agent. For example, the mAb and the at least one chemotherapeutic agent may be administered substantially simultaneously i.e. at the same time, using for example a combined dosage form or separate dosage forms. This form of administration may also be referred to as "concomitant" administration. Concurrent administration refers to administration of the active agents within the same general time period, for example on the same day(s) but not necessarily at the same time. For example, one active agent may require administration with food, while the other requires administration in the semi-fasting state. Alternate administration includes administration of one agent during a particular time period, for example over the course of a few days or a week, followed by administration of the other agent during a subsequent identical period of time, and then repeating the pattern for one or more cycles. Sequential or successive administration includes administration of one agent during a first time period, using one or more doses, followed by administration of the other agent during a second time period using one or more doses. An overlapping schedule may also be employed, which includes administration of the active agents on different days over the treatment period, not necessarily according to a regular sequence. Variations on these general guidelines may also be employed, according to the agents used and the condition of the subject.

Methods of the Invention

The mAbs of the invention are useful for treating a disease or disorder associated with heparanase activity in a subject in need thereof. In some embodiments there is provided use of the mAbs of the invention for preparation of a medicament for treating a disease or disorder associated with heparanase activity.

As used herein, the terms "heparanase activity", "heparanase enzymatic activity" or "heparanase catalytic activity" refer to an animal endoglycosidase hydrolyzing activity which is specific for heparin or heparan sulfate substrates, as opposed to the activity of bacterial enzymes (heparinase I, II and III) which degrade heparin or heparan sulfate by means of beta-elimination.

Heparanase activity which is inhibited or neutralized according to the present invention can be of either recombinant or natural heparanase. Such activity is disclosed, for example, in U.S. Pat. Nos. 6,177,545 and 6,190,875, which are incorporated by reference as if fully set forth herein. Methods for determining heparanase activity as well as antibodies neutralizing effect are known in the art. In some embodiments, heparanase neutralizing effect may be measured by activity assays as described herein (e.g., examples 1E and 3A). In another embodiments, the affinity of an antibody to a the heparan sulfate (HS) binding domain, such as the $Lys^{158}$-$Asp^{171}$ domain of human heparanase may be measured. In additional embodiments, the cellular uptake of heparanase may be measured.

As used herein, the term "associated with heparanase catalytic activity" refers to conditions which at least partly depend on the catalytic activity of heparanase. It is being understood that the catalytic activity of heparanase under many such conditions can be normal, yet inhibition thereof in such conditions will result in improvement of the affected individual.

The pharmaceutical composition according to the present invention may be administered as a stand-alone treatment or in addition to a treatment with any other therapeutic agent. According to a specific embodiment, antibodies according to the present invention are administered to a subject in need thereof as part of a treatment regimen in conjunction with at least one anti-cancer agent. The pharmaceutical composition according to the present invention may be administered together with other agents or separately.

As used herein to describe the present invention, "malignant proliferative disorder" "cancer", "tumor" and "malignancy" all relate equivalently to a hyperplasia of a tissue or organ. All types of tumors may be treated by the methods of the present invention. The tumors may be solid or non-solid.

According to some embodiments, the mAb of the invention or a composition comprising the same, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma (Weissmann et al., Proc Natl Acad Sci USA 113:704-709, 2016).

According to another embodiment, the proliferative disease is a solid malignancy including but not limited to carcinoma, sarcoma, glioma and melanoma. According to additional embodiments, the mAb of the invention or a composition comprising the same, can be used for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

It is to be therefore understood that the compositions of the invention are useful for treating or inhibiting tumors at all stages, namely tumor formation, primary tumors, tumor progression or tumor metastasis.

In another embodiment, mAb of the invention can be used for inhibition of angiogenesis, and are thus useful for the treatment of diseases and disorders associated with angiogenesis or neovascularization such as, but not limited to, tumor angiogenesis, opthalmologic disorders such as diabetic retinopathy and macular degeneration, particularly age-related macular degeneration, and reperfusion of gastric ulcer.

The mAb of the invention or any compositions thereof are useful for inhibiting or treating other cell proliferative diseases or disorders such as psoriasis, hypertrophic scars, acne and sclerosis/scleroderma, and for inhibition or treatment of other diseases or disorders such as polyps, multiple exostosis, hereditary exostosis, retrolental fibroplasia, hemangioma, and arteriovenous malformation.

Heparanase catalytic activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase catalytic activity (Vlodaysky, I. et at, Invasion & Metastasis 12, 112-127 (1992). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparanase released by platelets and macrophages is likely to be present in atherosclerotic lesions (Campbell, K. H. et al. Exp. Cell Res. 200, 156-167 (1992)). Thus, the mAb of the invention or any compositions thereof are also useful for inhibiting or treating autoimmune and inflammatory diseases Therefore, in a further embodiment, the compositions of the invention may be useful for treatment of or amelioration of inflammatory symptoms in any disease, condition or disorder where immune and/or inflammation suppression is beneficial such as, but not limited to, treatment of or amelioration of inflammatory symptoms in the joints (Li et al. Arthritis Rheum 2008, 58:1590-600), musculoskeletal and connective tissue disorders, or of inflammatory symptoms associated with hypersensitivity (Edovitsky et al. Blood 2005, 3609-16) allergic reactions, asthma, atherosclerosis (Planer et al. Plos ONE 2011; 6(4):e18370), otitis and other otorhinolaryngological diseases, dermatitis and other skin diseases, posterior and anterior uveitis, conjunctivitis, optic neuritis, scleritis and other immune and/or inflammatory ophthalmic diseases.

In another embodiment, the compositions of the invention are useful for treatment of or amelioration of an autoimmune disease such as, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis (Li et al. Arthritis Rheum 2008, 58:1590-600), scleroderma, thrombocytopenia, thyroiditis e.g. Hashimoto's disease, Sjbgren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pernphigoid, dennatitis herpetiformis, insulin dependent diabetes, inflammatory bowel disease, ulcerative colitis and Crohn's disease (Lerner et al, J Clin Invest 2011, 121:1709-21).

Still further, heparanase has been proposed to be involved in the pathogenesis of proteinuria by selectively degrading the negatively charged side chains of heparan sulfate proteoglycans within the glomerular basement membrane. A loss of negatively charged heparan sulfate proteoglycans may result in alteration of the permselective properties of the glomerular basement membrane, loss of glomerular epithelial and endothelial cell anchor points, and liberation of growth factors and potentially leading to different kidney disorders, such as, passive Heymann nephritis (PHN), and puromycin aminonucleoside nephrosis (PAN). As described by Levidiotis, V. et al. (Levidiotis, V. et al., J. Am. Soc.

Nephrol. 15, 68-78 (2004)), a polyclonal antibody against heparanase, significantly reduced proteinuria without affecting the histologic appearance of glomeruli and the immune mechanisms, which give rise to PHN, and therefore, inhibition of heparanase may be used to reduce proteinuria. Notably, the heparanase inhibitor SST0001 reduced proteinuria associated with type 1 and type 2 diabetes (Gil et al. Diabetes 2012; 61: 208-16). Therefore, in another embodiment, the mAbs of the invention or compositions thereof are useful for treatment of or amelioration of any kidney disorder.

In another embodiment, the mAbs of the invention or compositions thereof are useful for treatment of or amelioration diabetic nephropathy. In another embodiment, the mAbs of the invention or compositions thereof are useful for treatment of or amelioration of type-1 diabetes (Ziolkowski et al. 2012; 122:132-41).

The term "mammal" means any mammal, including pet animals, such as dogs and cats; farm animals, such as pigs, cattle, sheep, and goats; laboratory animals, such as mice and rats; primates, such as monkeys, apes, and chimpanzees; and preferably, humans.

Having now generally described the invention, the same will be more readily understood through reference to the following examples, which are provided by way of illustration and are not intended to be limiting of the present invention.

EXAMPLES

Methods of the Invention and Determination of CDRs

Generation of monoclonal antibodies (mAb). BALB/c mice were immunized with 50 µg of KKDC peptide coupled to KLH in complete Freund's adjuvant (CFA; Sigma), followed by five injections (50 µg) of KLH-KKDC in incomplete Freund's adjuvant (IFA) every 2 weeks. Following tail vein injection splenocytes were isolated, fused with NSO myeloma cells and hybridomas were screened for their ability to bind BSA-KKDC or heparanase by ELISA, essentially as described (Gingis-Velitski et al. Faseb J 2007; Levy-Adam et al. J Biol Chem 2010; 285(36):28010-9; Shafat et al. Biochem Biophys Res Commun 2006; 341(4): 958-63). Positive hybridomas were selected, expanded and cloned. Hybridoma subclass was determined by isotyping kit according to the manufacturer's (Serotec, Oxford, UK) instructions. mAb 9E8 was characterized as IgM and was purified by affinity chromatography on mannan binding protein according to the manufacturer's (Pierce Biotechnology, Rockford, Ill.) instructions (Weissmann et al, 2016, Proc Natl Acad Sci USA 113:704-709). Purified antibody was resolved by SDS-PAGE, heavy and light chain protein bands were extracted and sequenced. The corresponding nucleotide sequences were then revealed, and the genes were amplified by RT-PCR and cloned using the following primers:

```
Hf24-V-Kappa-FOR primer:
5' gatattgtgatgactcaggctgc;      (SEQ ID. No. 17)

Mouse-C-Kappa-REV primer:
5' gtagaagttgttcaagaagc;         (SEQ ID. No. 18)

X24.2.50-VH-FOR:
gaggtgaagcttctcgagtctgg;        (SEQ ID. No. 19)

Mouse-C-Mu-REV:
gggcaggaagtcccgggccaggc.        (SEQ ID. No. 20)
```

Nucleotide and amino acid sequences of mAb 9E8 are shown in Table 1. Mouse IgM (Sigma) was used as control. Anti-heparanase 1453 polyclonal antibody was raised against the entire 65 kDa latent heparanase protein (Zetser et al. J Cell Sci 2004; 117(11):2249-58).

TABLE 1

Nucleotide and amino acid sequences of mAb 9E8

| Variable Chain | Sequence | | SEQ ID NO: |
|---|---|---|---|
| Variable Heavy Chain | Amino acid sequence | EVKLLESGGGLVQPGGSLKLSCAASGFDFSRY WMSWVRQAPGKGLEWIGEINPDSSTINYTPSL KDKFIISRDNAKNTLYLQMSKVRSEDTALYYC ARRGYEGNYAMDYWGQGTSVTVSSESQSFPNV FPLVSCESPLSDKNLVAMGCLAR | 7 |
| | Nucleic acid sequence | GAGGTGAAGCTTCTCGAGTCTGGAGGTGGCCT GGTGCAGCCTGGAGGATCCCTGAAACTCTCCT GTGCAGCCTCAGGATTCGATTTTAGTAGATAC TGGATGAGTTGGGTCCGGCAGGCTCCAGGGAA AGGGCTAGAATGGATTGGAGAAATTAATCCAG ATAGCAGTACGATAAACTATACGCCATCTCTA AAGGATAAATTCATCATCTCCAGAGACAACGC CAAAAATACGCTGTACCTGCAAATGAGCAAAG TGAGATCTGAGGACACAGCCCTTTATTACTGT GCAAGACGGGGTACGAGGGTAACTATGCTAT GGACTACTGGGGTCAAGGAACCTCAGTCACCG TCTCCTCAGAGAGTCAGTCCTTCCCAAATGTC TTCCCCCTCGTCTCCTGCGAGAGCCCCCTGTC TGATAAGAATCTGGTGGCCATGGGCTGCCTGG CCCGGG | 9 |
| | CDR-H1 | GFDFSRY | 1 |
| | CDR-H1 | GFDFSRYWMS | 13 |
| | CDR-H2 | INPDSSTI | 2 |
| | CDR-H2 | EINPDSSTINYTPSLKD | 14 |
| | CDR-H3 | RGYEGNYAMDY | 3 |
| | CDR-H3 | ARRGYEGNYAMDY | 12 |
| Variable Light Chain | Amino acid sequence | DIVMTQAAPSVPVTPGESVSISCRSSKSLLHS NGNTYLYWFLQRPGQSPQLLIYRMSNLASGVP DRFSGSGSGTAFTLRISRVEAEDVGVYYCMQH LEYPFTFGSGTKLEIKRADAAPTVSIFPPSSE QLTSGGASVVCFL | 8 |
| | CDR-L1 | KSLLHSNGNTY | 4 |
| | CDR-L1 | RSSKSLLHSNGNTYLY | 15 |
| | CDR-L2 | RMS | 5 |
| | CDR-L2 | RMSNLAS | 16 |
| | CDR-L3 | MQHLEYPFT | 6 |
| | Nucleic acid sequence | GATATTGTGATGACTCAGGCTGCACCCTCTGT ACCTGTCACTCCTGGTGAGTCAGTATCCATCT CCTGCAGGTCTAGTAAGAGTCTCCTGCATAGT AATGGCAACACTTACTTGTATTGGTTCCTGCA GAGGCCAGGCCAGTCTCCTCAGCTCCTGATAT ATCGGATGTCCAACCTTGCCTCAGGAGTCCCA GACAGGTTCAGTGGCAGTGGGTCAGGAACTGC TTTCACACTGAGAATCAGTAGAGTGGAGGCTG AGGATGTGGGTGTTTATTACTGTATGCAACAT CTAGAATATCCATTCACGTTCGGCTCGGGGAC AAAGTTGGAAATAAAACGGGCTGATGCTGCAC CAACTGTATCCATCTTCCCACCATCCAGTGAG CAGTTAACATCTGGAGGTGCCTCAGTCGTGTG CTTCTTGAA | 10 |

Cells and cell culture. Daudi, Ramos, Raji, and SU-DHL-6 human B lymphoma cells were purchased from the American Type Culture Collection (ATCC, Manassas, Va.). OCI-LY-19 cell line was purchased from DSMZ (Braunschweig, Germany). ESb and E1-4 mouse lymphoma cells have been described previously (Vlodaysky I., et al., 1983, Cancer Res 43:2704-2711). Cells were grown in RPMI medium (Biological Industries, Beit Haemek, Israel) supplemented with 10% fetal calf serum and antibiotics. Raji cells were infected with luciferase gene construct and a cell clone exhibiting high luciferase activity was selected for in vivo experiments. B16-BL6 mouse melanoma, rat C6 glioma and U87 human glioma cells have been described previously (Edovitsky E, et al., 2004, J Natl Cancer Inst 96(16):1219-12308). Luciferase-labelled CAG myeloma cells were kindly provided by Gera Neufeld (Rappaport Faculty of Medicine, Technion, Israel). LM2-4 human breast carcinoma cells were kindly provided by Dr Robert Kerbel (University of Toronto, Toronto, Ontario, Canada) (Weissmann et al, 2016, Proc Natl Acad Sci USA 113:704-709).

Antibodies and reagents. Anti-heparanase polyclonal antibody #1453 has been described previously (Zetser A, et al. 2004, *J Cell Sci* 117(11):2249-2258). Rat anti-mouse CD31 was from Dianova (Hamburg, Germany); Rat anti-mouse CD45 was purchased from BioLegends (San Diego, Calif.); Anti-human HLA and anti-Ki67 monoclonal antibodies were purchased from Abcam (Cambridge, UK). Anti-cleaved caspase 3 was purchased from Cell Signaling (Beverly, Mass.). The heparanase and angiogenesis inhibitor PG545 was kindly provided by Progen Pharmaceuticals (Brisbane, Australia) (Dredge K, et al. 2011, Br J Cancer 104(4):635-642). The heparanase inhibitor SST0001 (Roneparstat; non-anticoagulant glycol-split heparin) was kindly provided by Sigma Tau Research Switzerland (Mendrisio, Switzerland) (Pisano C, et al., 2014, Biochem Pharmacol 89(1):12-19; Ritchie J P, et al. 2011, Clin Cancer Res 17(6):1382-1393).

Cell lysates, heparanase activity and protein blotting. Preparation of cell lysates, protein blotting, and measurement of heparanase enzymatic activity were carried out as described (Vlodaysky I, et al. 1999, Nature Med 5(7):793-802; Arvatz et at, 2011, FASEB J 24(12):4969-4976). For inhibition studies, highly purified constitutively active GS3 heparanase (200 ng) (Nardella C, et al. 2004, Biochemistry 43(7):1862-1873) was pre-incubated with the indicated antibody (2 µg/ml) for 30 min on ice under neutral pH conditions (pH 7.2) before being added to $^{35}$S-labelled ECM, used as a naturally produced substrate for heparanase (Weissmann et al, 2016, Proc Natl Acad Sci USA 113:704-709). Likewise, cell lysates or tumor extracts were incubated (12 h, 37° C., pH 6.0) with the labeled ECM and sulfate labeled degradation fragments released into the incubation medium were analyzed by gel filtration on a Sepharose CL-6B column. Degradation fragments of HS side chains are eluted from Sepharose 6B at 0.5<Kav<0.8 (peak II, fractions 17-30). Nearly intact sulfate labeled HSPGs are eluted just after the void volume (Kav<0.2, peak I, fractions 1-10). These high molecular weight products are released by proteases that cleave the HSPG core protein (Vlodaysky I, et al. 1999, Nature Med 5(7):793-802; Weissmann et al, 2016, Proc Natl Acad Sci USA 113:704-709). Each experiment was performed at least three times and the variation in elution positions (Kav values) did not exceed ±15%.

Cell invasion. Matrigel invasion assay was performed using modified Boyden chambers with polycarbonate Nucleopore membrane (Corning, Corning, N.Y.), essentially as described (17). Briefly, filters (6.5 mm in diameter, 8 µm pore-size) were coated with Matrigel (30 µl); Cells (2×10$^5$) in 100 µl of serum-free medium were seeded in triplicate on the upper part of each chamber, and the lower compartment was filled with 600 µl medium supplemented with 10% FCS. After incubation for 5 h at 37° C. in a 5% $CO_2$ incubator, non-invading cells on the upper surface of the filter were wiped with a cotton swab, and migrated cells on the lower surface of the filter were fixed, stained with 0.5% crystal violet (Sigma) and counted by examination of at least seven microscopic fields.

Experimental metastasis. B16 BL6 mouse melanoma (2×10$^5$) or LM2-4 human breast cancer cells (2×10$^6$) were injected into the tail vein of C57/BL mice or SCID/Beige mice (respectively) together with the indicated compound, essentially as described (Hostettler N, et al. 2007, FASEB J 21(13):3562-3572). Lungs were harvested 18 days thereafter and metastases occurrence was determined following fixation by gross inspection and histology (Weissmann et al, 2016, Proc Natl Acad Sci USA 113:704-709).

Tumorigenicity. Luciferase-labelled CAG myeloma (5×10$^6$) or Raji lymphoma (1×10$^6$) cells were injected into the tail vein of NOD/SCID mice (n=5). Mice were treated with PG545 (20 mg/kg, once weekly), mAb 9E8 (600 µg/mouse) every other day starting one day following cell inoculation and tumor growth was examined by IVIS imaging. At termination, mice were sacrificed, the backbones were excised, fixed in formalin and following de-calcification with 10% EDTA solution were embedded in paraffin and subjected to histological and immunohistochemical analyses essentially as described (Weissmann et al, 2016, Proc Natl Acad Sci USA 113:704-709). Dose of 25-30 mg/kg (i.e., 500-600 µg mAb/mouse) is typical in cancer restraining experiments (Van Looy T, et al. 2015, Transl Oncol 8(2):112-118).

Lymphoma cells were also inoculated subcutaneously at the right flank of 6-weeks-old NOD/SCID mice (human cell lines) or C57BL/6 mice (E1-4 mouse lymphoma cells) (n=7). Mice were treated with heparanase inhibitors (PG545; SST0001) or neutralizing antibodies and xenografts size was determined by externally measuring the tumors in 2 dimensions using a caliper. At the end of the experiment, mice were sacrificed; tumor xenografts were removed, weighed and fixed for histological and immunohistochemical analyses (Weissmann et al, 2016, Proc Natl Acad Sci USA 113:704-709). ESb mouse T-lymphoma cells (5×10$^5$) were similarly inoculated subcutaneously into SCID mice and spontaneous metastasis to the liver (Vlodaysky et al., 1983, Cancer Res 43:2704-2711) was examined after 3 weeks of treatment with PG545 or the neutralizing mAb, as described above. All animal experiments were approved by the Animal Care Committee of the Technion, Haifa, Israel.

IVIS imaging. Bioluminescent imaging of the luciferase-expressing tumors was performed with a highly sensitive, cooled charge coupled device (CCD) camera mounted in a light-tight specimen box (IVIS; Xenogen Corp., Waltham, Mass.). Briefly, mice were injected intraperitoneally with D-luciferin substrate at 150 mg/kg, anesthetized and placed onto a stage inside the light-tight camera box, with continuous exposure to isoflurane (EZAnesthesia, Palmer, Pa.). Light emitted from the bioluminescent cells was detected by the IVIS camera system with images quantified for tumor burden using a log-scale color range set at 5×10$^4$ to 1×10$^7$ and measurement of total photon counts per second (PPS) using Living Image software (Xenogen) (Weissmann et al, 2016, Proc Natl Acad Sci USA 113:704-709).

Class switch of monoclonal 9E8 IgM antibodies to IgG. We applied a "cloning free" approach to generate antibodies with altered heavy chain isotype by mimicking the germinal center reaction in antibody-secreting hybridoma cells (Su Y C et al., 2014, MAbs 6:1069-83). Briefly, hybridoma clone 9E8 producing the anti-heparanase IgM mAbs was stably transfected (electroporation) with a construct encoding for AID (activation-induced cytidine deaminase) and GFP reporter (and containing Lox-Cre recombination sites to allow removal of the AID-GFP upon obtaining the desirable clones) (Su Y C et al., 2014, MAbs 6:1069-83). The transfected cells were subjected to selection (puromycin) and expansion to allow immunoglobulin somatic hypermutation (SHM) and class switch recombination (CSR) of the immunoglobulin genes (Su Y C et al., 2014, MAbs 6:1069-83). This was followed by multiple rounds of selection with biotin-labeled heparanase (detected by fluorescent streptavidin) and sorting (FACS) for surface IgG expressing cells that bind heparanase. This procedure yielded hybridoma that secretes affinity maturated anti-heparanase antibodies that were classified as IgG1.

Statistics. Data are presented as mean±SE. Statistical significance was analyzed by one way ANOVA (Tukey post test) or two-tailed Student's t-test. The value of P<0.05 is considered as significant. All animal experiments were approved by the Animal Care Committee of the Technion, Haifa, Israel.

Example 1

Inhibition of Lymphoma Xenograft Growth by a Potent Heparanase Inhibitor, PG545

Figure 1B:
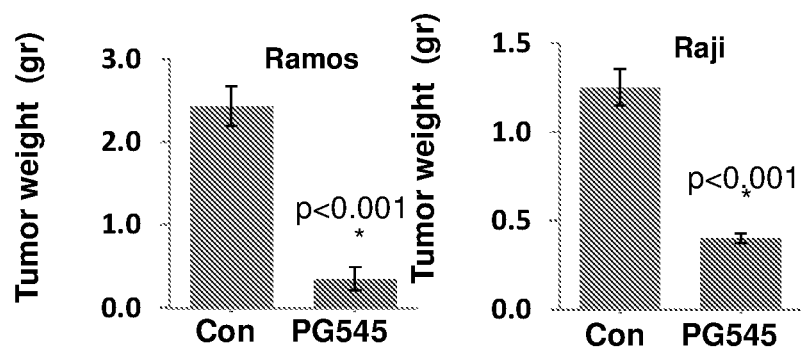
FIG. 1B (left and right), FIG. 1C (left and right) and FIG. 1D (left and right) are bar graphs representing the inhibitory effect of compound PG545 on human lymphoma tumor development in SCID/NOD mice.
Figure 1C:
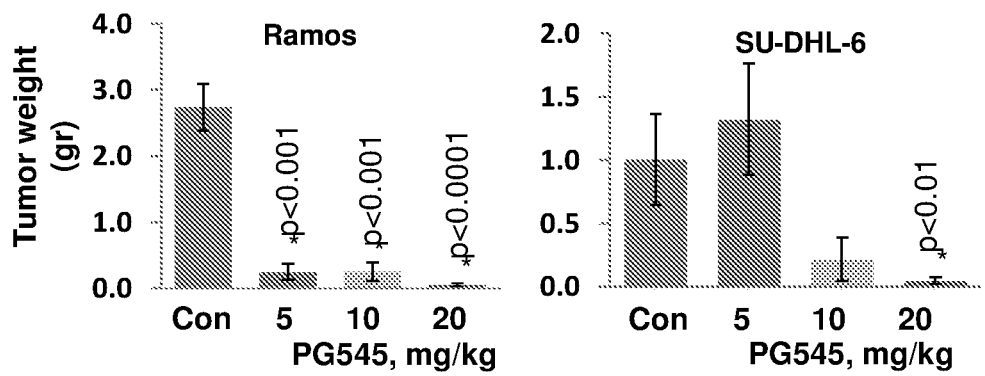
FIG. 1E (upper and lower panel) is a line graph representing the activity of heparanase in Raji lymphoma cells maintained in culture vs. Raji tumors in SCID mice in the absence and presence of PG545. Note that Raji cells lack heparanase activity whereas tumor xenografts exhibit typical heparanase activity.

Human lymphoma biopsy specimens were subjected to immunostaining. As can be seen, it was found that heparanase is expressed in both follicular (FIG. 1A, left) and diffuse (FIG. 1A, right) lymphomas, representing an indolent and aggressive disease, respectively. In order to examine the involvement of heparanase in lymphoma in greater detail, immunocompromised NOD/SCID mice were inoculated with human lymphoma cell lines and treated the mice with a potent heparanase inhibitor, PG545 (Dredge K, et al. 2011, Br J Cancer 104(4):635-642). As shown, the growth of tumor xenografts produced by Burkitt's (Ramos, Raji, Daudi), diffused (OCI-LY-19), and follicular (SU-DHL-6) lymphoma cells was markedly attenuated by PG545 (FIG. 1B) in a dose-dependent manner (FIG. 1C). Inhibition of tumor xenograft growth was most effective when PG545 was administrated upon cell inoculation (FIG. 1B), but significant inhibition was also observed when PG545 was administrated once the lesions became palpable (FIG. 1D) (Weissmann et al, 2016, Proc Natl Acad Sci USA 113:704-709).

Figure 1D:
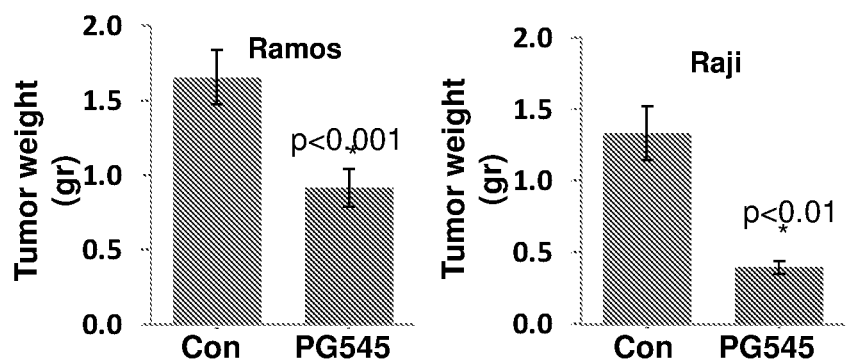
Figure 1E:
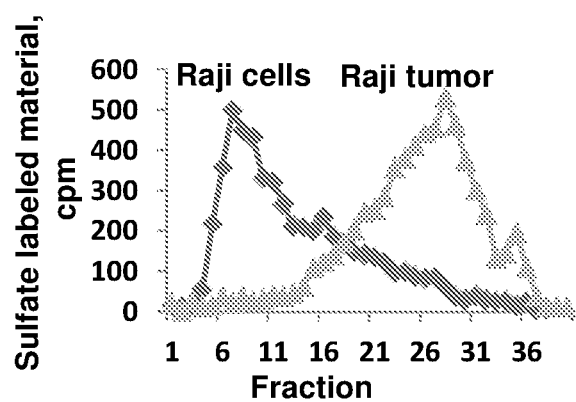
Figure 1E:
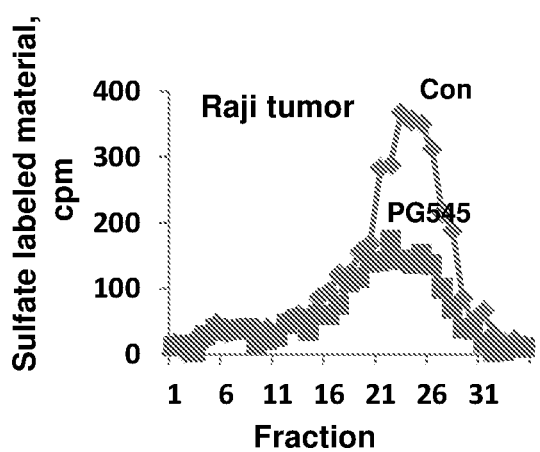

Inhibition of heparanase originating from the tumor microenvironment is sufficient to restrain lymphoma growth. Despite the lack of heparanase activity in Raji cells (FIG. 1E, upper panel, Raji cells,) due to gene methylation (Shteper P J, et al. 2003, Oncogene 22(49):7737-7749), tumor xenografts produced by Raji cells exhibit typical heparanase activity (FIG. 1E, upper panel, Raji tumor), suggesting that heparanase-positive cells derived from the host populate the tumor microenvironment. Inhibition of Raji tumor xenografts by PG545 (FIG. 1), in a manner similar to the other lymphoma cell lines, is therefore due to inhibition of heparanase activity contributed by the tumor microenvironment (FIG. 1E, lower panel). This implies that the host contributes a significant amount of heparanase, and that inhibition of this fraction is sufficient to attenuate tumor growth. Indeed, tumor xenografts developed by cells that lack heparanase enzymatic activity (i.e., E1-4) but fail to attract heparanase-positive cells to the tumor are not inhibited by PG545 (Weissmann et al, 2016, Proc Natl Acad Sci USA 113:704-709).

Detailed Description of FIGS. 1A-1E

A. Specimens of human follicular (FIG. 1A, left panel) and diffuse (FIG. 1A, right panel) B-cell lymphomas were subjected for immunostaining applying anti-heparanase antibody. Shown are heparanase-negative (upper panels) and -positive (lower panels) lymphoma biopsy specimens. FIG. 1B. The indicated lymphoma cells ($5\times10^6$) were implanted subcutaneously in NOD/SCID mice (n=7) and mice were administered with PG545 (IP, 20 mg/kg, once weekly, starting one day after cell inoculation), or control vehicle (PBS; Con). At termination, tumors were removed, weighted and embedded in paraffin for histological and immunohistochemical analyses. Mice were similarly inoculated with the indicated lymphoma cells and were treated with the indicated concentration of PG545 (mg/kg once a week; FIG. 1C) or were treated with PG545 (20 mg/kg once a week) once the tumors became palpable (FIG. 1D). Shown are average (±SE) tumor weight (gr.). FIG. 1E. Lysates of Raji cells and extracts of tumor xenografts produced by Raji cells were applied onto dishes coated with sulfate-labelled ECM and heparanase enzymatic activity was determined as described (Vlodaysky I, et al. 1999, Nature Med 5(7):793-802). Note that Raji cells lack heparanase activity whereas tumor xenografts exhibit typical heparanase activity. Extracts of control (Con) and PG545-treated tumor xenografts produced by Raji cells were applied onto dishes coated with sulfate labelled ECM and heparanase activity was determined as above (lower panel). Note that PG545 inhibits heparanase activity in tumor xenografts produced by Raji cells.

Example 2

Inhibition of Heparanase Activity and Lymphoma Xenograft Growth by Heparanase-Neutralizing Polyclonal Antibody #1453

Figure 2A:
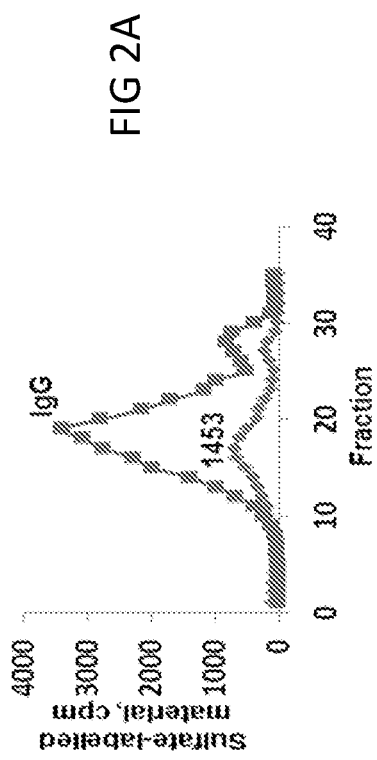
FIG. 2A is a line graph representing the inhibitory effect of Ab #1453 on the enzymatic activity of recombinant heparanase.
Figure 2B:
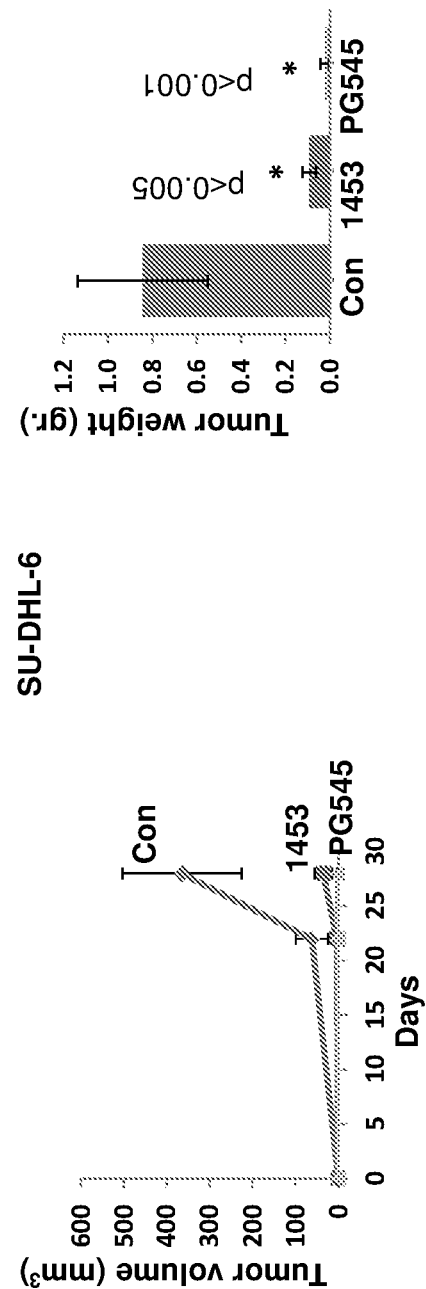
FIG. 2B (left and right) is a line graph representing the effect of Ab #1453 or compound PG545 on lymphoma tumor growth (volume (left graph) and weight (right graph)) in SCID mice.
Figure 2C:
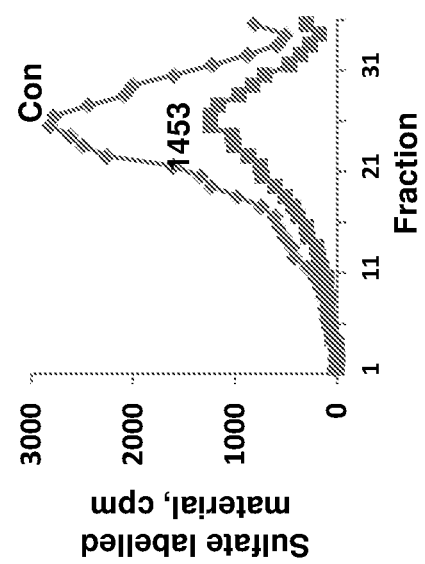
FIG. 2C is a line graph representing heparanase enzymatic activity in tumor extracts derived from mice treated with Ab #1453 vs. untreated control mice.
Figure 2D:
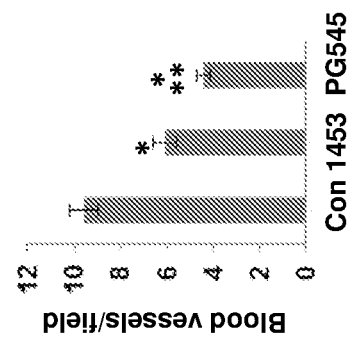
FIG. 2D (left and right) represents micrographs and bar graph showing the effect of Ab #1453 or PG545 on lymphoma tumor size (hematoxilin & eosin), tumor angiogenesis (anti CD31, blood vessels) and apoptosis (anti cleaved caspase-3).
Figure 2D:
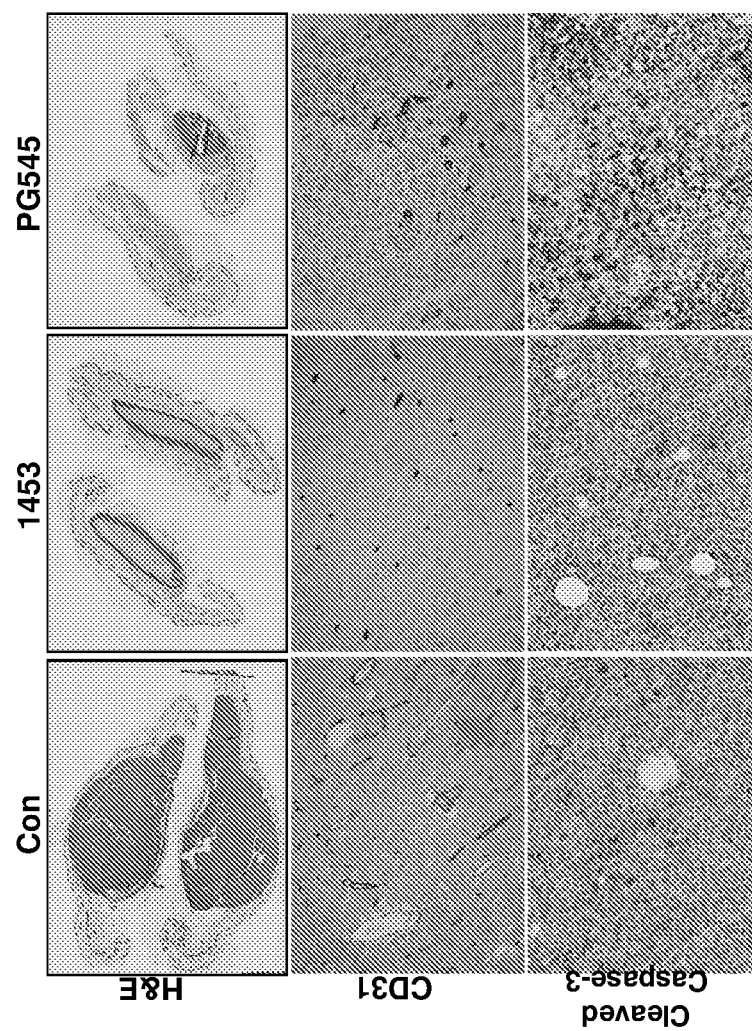

While PG545 appears as a potent inhibitor that attenuates the progression of several carcinomas (Dredge K, et al. 2011, *Br J Cancer* 104(4):635-642) and lymphomas (FIG. 1), it also exhibits heparanase-unrelated properties and impedes the signaling of HS-bound growth- and angiogenesis-promoting factors (Ferro V, et al. 2012, J Med Chem 55(8):3804-3813). In order to evaluate the role of heparanase in lymphoma growth in a more specific manner, a polyclonal antibody (#1453) that neutralizes heparanase enzymatic activity was used (FIG. 2A). As expected, cell invasion and tumor metastasis were significantly inhibited by this antibody (Weissmann et al, 2016, Proc Natl Acad Sci USA 113:704-709). Moreover, growth of tumor xenografts produced by U87 glioma cells, shown previously to be strictly dependent on heparanase levels (Arvatz G, et al., 2011. FASEB J 24(12):4969-4976), was inhibited by antibody #1453 as a single agent and even stronger inhibition was obtained when antibody #1453 was combined with SST0001, a heparin mimetic heparanase inhibitor (Ritchie J P, et al. 2011, SST0001, Clin Cancer Res 17(6):1382-1393). In addition, the growth of tumor xenografts produced by SU-DHL-6 lymphoma cells was markedly inhibited by antibody #1453 (FIG. 2B), associating with decreased heparanase activity in these tumors (FIG. 2C). Antibody #1453 similarly inhibited the growth of tumor xenografts produced by Ramos, Raji, and OCI-LY-19 lymphoma cells (data not shown). Moreover, treatment with antibody #1453 resulted in smaller tumors that were highly necrotic (FIG. 2D, upper panels) and exhibited reduced blood vessel density (FIG. 2D, second panels; CD31). Unlike PG545, Ab #1453 does not appear to enhance apoptotic cell death evident by staining for cleaved caspase 3 (FIG. 2D, lower panels), suggesting that these treatments inhibit tumor growth by different mechanisms. These results imply with greater confidence that heparanase enzymatic activity promotes lymphoma tumor growth (Weissmann et al, 2016, Proc Natl Acad Sci USA 113:704-709).

Detailed Description of FIGS. 2A-2D

FIG. 2A. Purified recombinant active heparanase (200 ng) was pre-incubated with control rabbit IgG (2 µg/ml; ■) or Ab #1453 (2 µg/ml; ♦) for 2 h in serum-free RPMI medium on ice. The mixture was then applied onto dishes coated with $^{35}$S-labeled ECM and heparanase enzymatic activity was determined as described under "Materials and Methods". FIG. 2B. SU-DHL-6 cells (5×106) were implanted subcutaneously in SCID mice (n=7) and mice were administered with Ab #1453 (250 µg/mouse; every other day), PG545 (20 mg/kg; once a week) or control vehicle (PBS) and tumor growth was inspected over time (FIG. 2B, left panel). At termination, tumors were harvested, weighted (FIG. 2B, right panel) and cut into two portions; one portion was lysed and subjected to determination of heparanase activity (FIG. 2C) while the other portion was fixed in formalin and subjected to histological (FIG. 2D, upper panel) and immunohistochemical analyses applying anti CD31 (FIG. 2D, second panels) and anti-cleaved caspase 3 (FIG. 2D, lower panels) antibodies. Blood vessels density was quantified by counting the number of CD31-positive vessels per field and is presented graphically at the right second panel. At least 25 fields of each treatment were counted. Original magnifications: upper panel x1; second and third panels x20. *p=4.5× 10–6 and 1.2×10–8 for Con vs. 1453 and Con vs. PG, respectively; **p=0.01 for 1453 vs. PG.

Example 3

Inhibition of Heparanase Uptake, Processing, Enzymatic Activity and Lymphoma Metastasis by Heparanase-Neutralizing Monoclonal Antibody 9E8

Figure 3A:
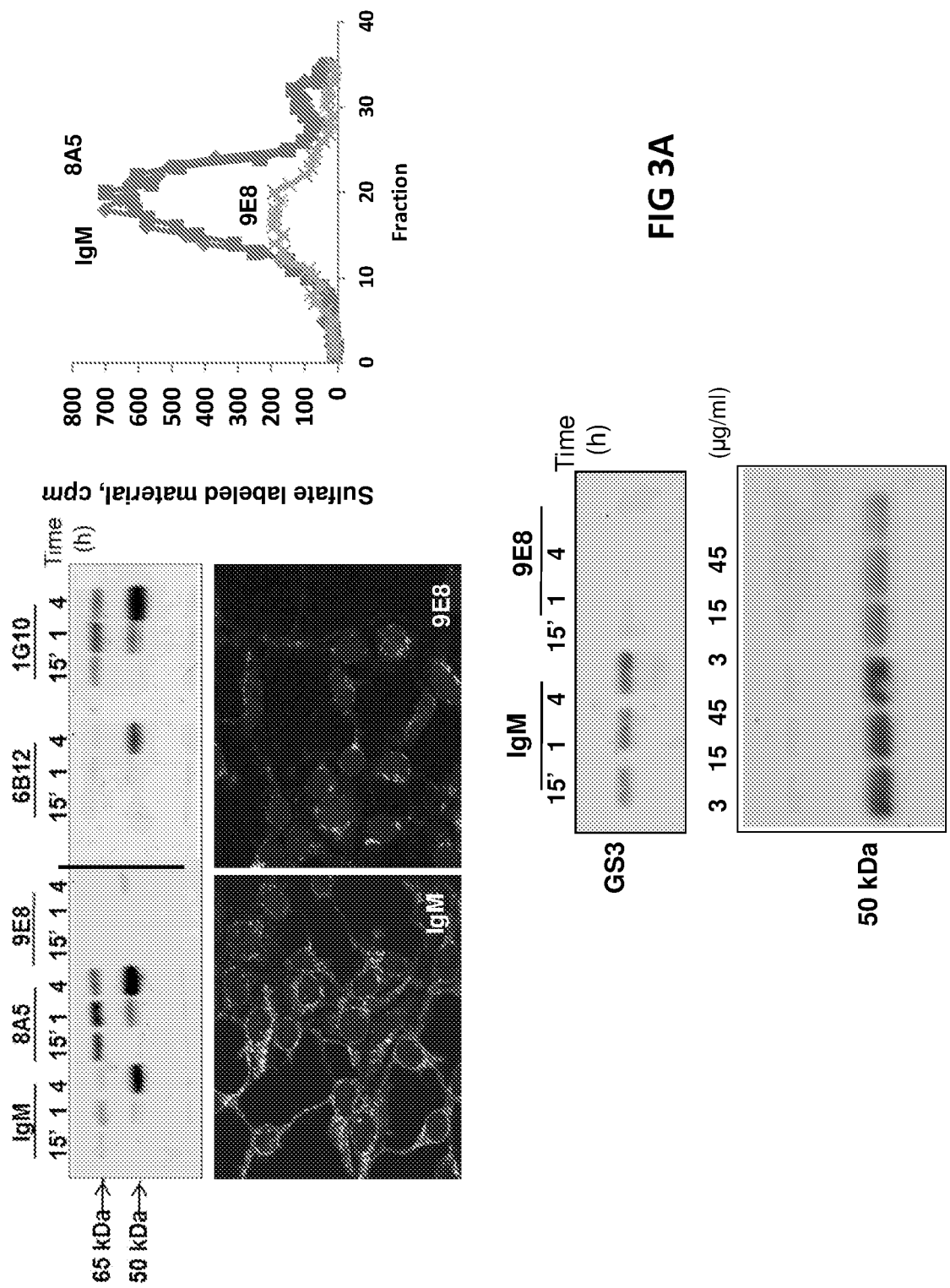
FIG. 3A (upper panel, second panel, third panel, fourth panel and lower panel) depicts the effect of mAb 9E8 in decreasing heparanase cellular uptake, processing (immunoblot) and content (immunofluorescent micrographs) compared to control IgM or anti-heparanase mAb 8A5, 6B12 or 1G10. The lower panel is a line graph representing the effect of mouse IgM (♦), mAb 8A5 (■) or, mAb 9E8 (x) on the enzymatic activity of recombinant heparanase.
Figure 5A:
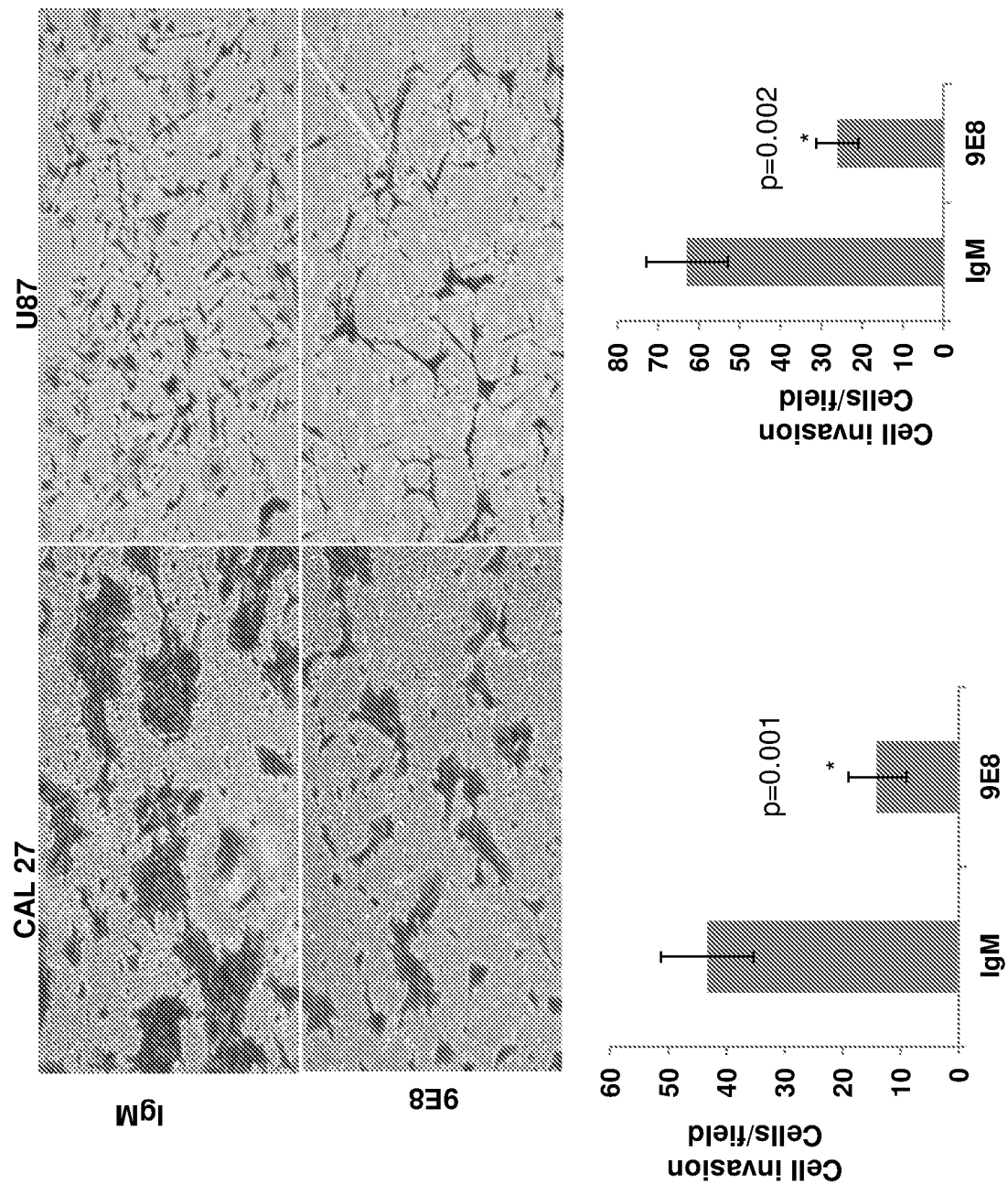
FIG. 5A (upper and lower) shows the inhibitory effect of mAbs 9E8 on human Cal-27 tongue carcinoma and U87 glioma cell invasion. The number of invading cells per high power field is shown graphically at the lower panels.
Figure 5B:
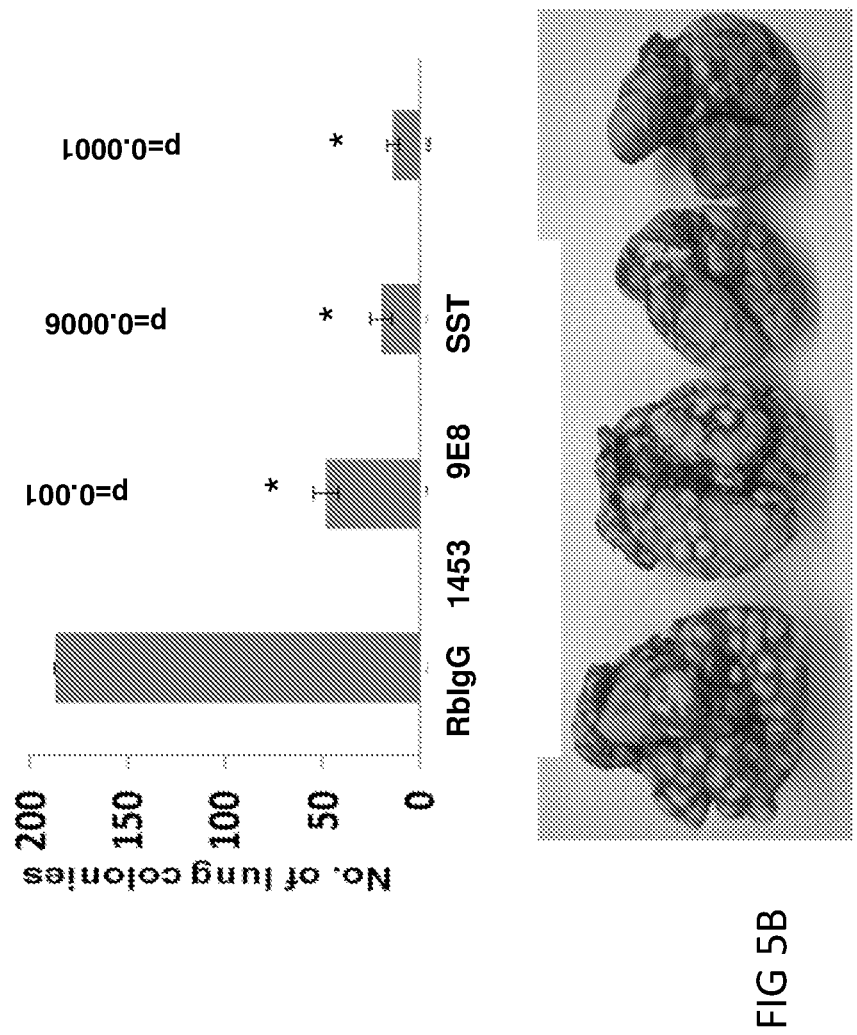
FIG. 5B (upper and lower) shows the inhibitory effect of Ab #1453, mAb 9E8 or compound SST0001 on mouse B16 melanoma experimental lung metastasis.
Figure 5C:
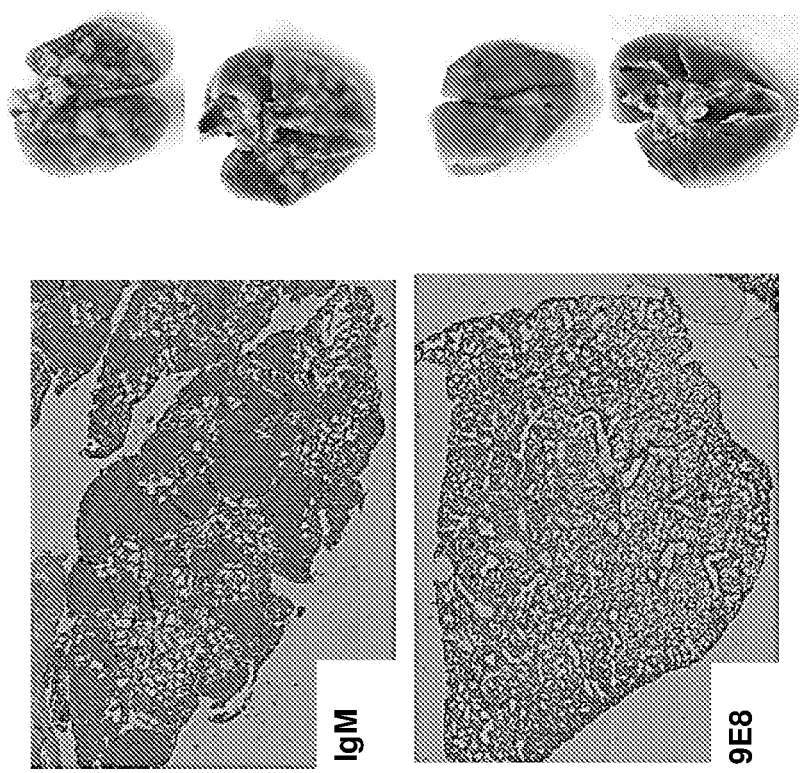
FIG. 5C (right and left panels) shows the inhibitory effect of mAb 9E8 on mouse LM2-4 human breast carcinoma experimental lung metastasis.

Development of heparanase-neutralizing monoclonal antibodies: In order to target heparanase activity even more specifically, a panel of monoclonal antibodies (mAb) directed against the KKDC peptide ($Lys_{158}$-$Asn_{171}$) which comprises the substrate (HS)-binding domain of heparanase (Levy-Adam F, et al. 2005, J Biol Chem 280(21):20457-20466) were developed. In order to validate that the resulting antibodies target the heparin/HS binding domain, cellular uptake of latent 65 kDa heparanase in the absence or presence of the various newly generated mAbs was tested. This system appeared most relevant because previous studies have shown that heparanase uptake is HS-dependent (Gingis-Velitski S, et al. 2004. J Biol Chem 279(42):44084-44092). Heparanase uptake and processing, evident by accumulation of the 50 kDa active subunit, were readily observed in cells incubated with control mouse IgM or anti-heparanase mAb 8A5, 6B12 or 1G10 (FIG. 3A). In striking contrast, heparanase uptake was markedly decreased in the presence of mAb 9E8 (FIG. 3A, upper panel). Similarly, uptake of the constitutively active heparanase (GS3) was inhibited profoundly by mAb 9E8 (FIG. 3A, third panel). Furthermore, incubation of cells over-expressing heparanase with mAb 9E8 resulted in a marked decrease in the intracellular content of heparanase evident by immunofluorescent staining (FIG. 3A, second panels) and immunoblotting (FIG. 3A, fourth panel), in agreement with the notion that intracellular processing of heparanase into its active (50+8 kDa) form occurs following uptake of the secreted 65 kDa latent protein (Gingis-Velitski S, et al. 2004. J Biol Chem 279(42): 44084-44092). Importantly, mAb 9E8 neutralizes heparanase enzymatic activity to magnitude comparable with the polyclonal antibody #1453 (FIG. 3A, lower panel) and inhibits cell invasion and tumor metastasis, the hallmarks of heparanase activity (FIG. 5A-C). We further employed a model of spontaneous metastasis and found that the survival of mice inoculated with highly metastatic ESb mouse T-lymphoma cells is prolonged by PG545 (FIG. 3B) associating with reduced liver metastasis. Moreover, liver metastasis of ESb cells was inhibited 4-5 fold by mAb 9E8 (FIG. 3C). The availability of highly specific heparanase-neutralizing mAbs led to the conclusion that heparanase enzymatic activity is required for cell invasion and tumor metastasis.

Figure 3B:
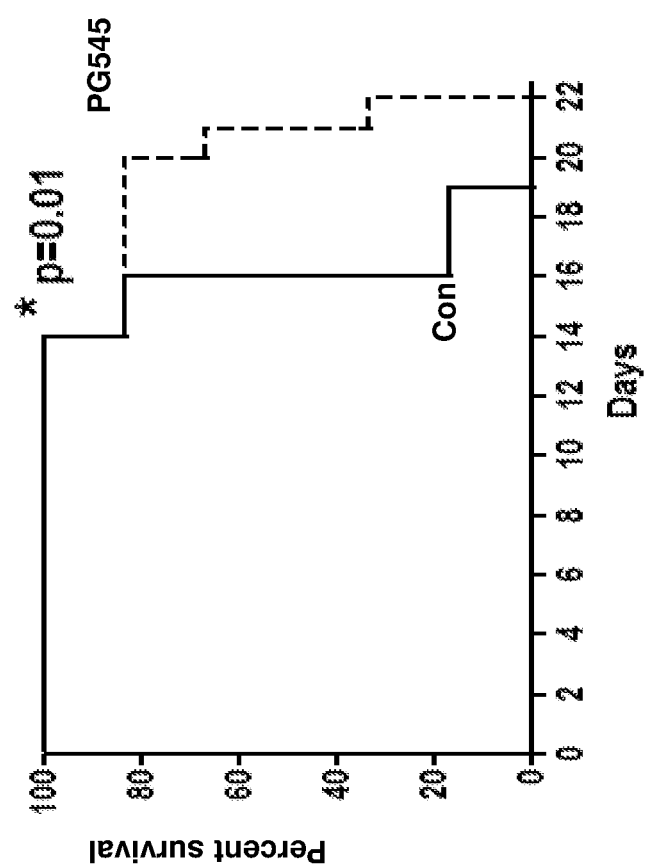
FIG. 3B depicts the inhibitory effect of mAbs 9E8 on liver metastasis of mouse lymphoma cells.
Figure 3C:
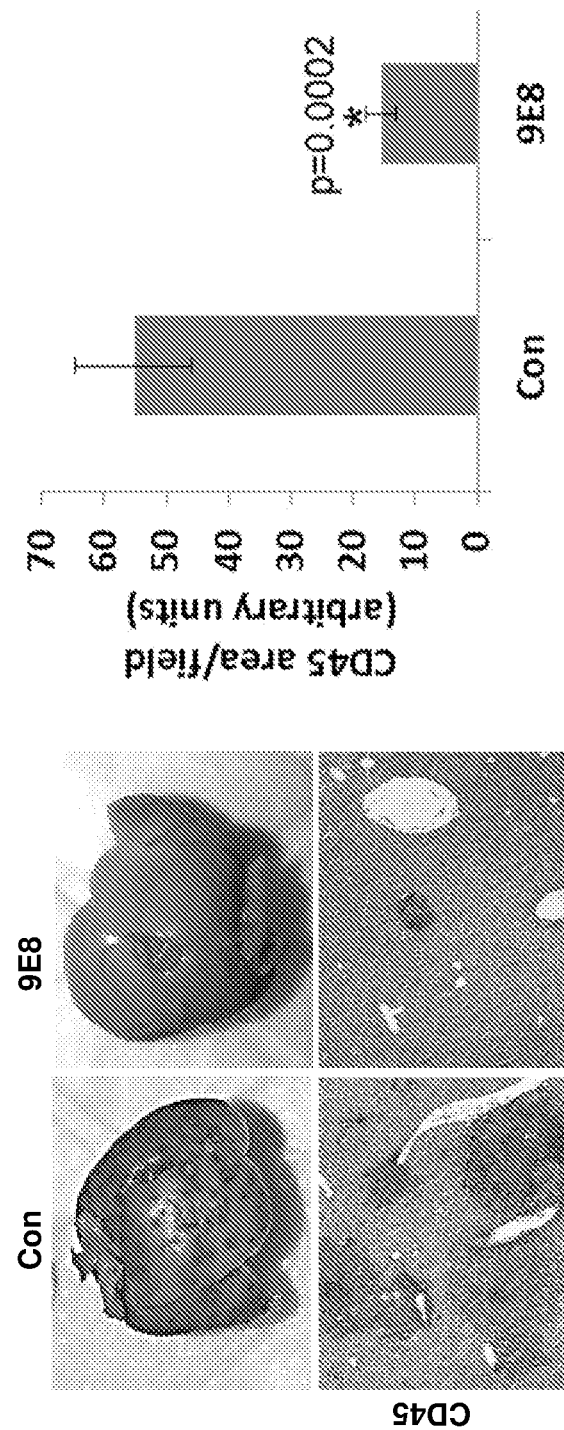
FIG. 3C (upper, second and lower panels) shows livers of mice treated with mAb 9E8 were removed after three weeks; photographed (upper panels), and five micron sections of formalin-fixed, paraffin-embedded liver tissue were subjected to immunostaining applying anti-CD45 antibody (second panels) and a bar graph (Lower panel).

Detailed Description of FIGS. 3A-3C

FIG. 3A. HEK 293 cells were incubated with latent 65 kDa (upper panel) or GS3 constitutively active heparanase (1 µg/ml; third panel) and the indicated mAbs (10 µg/ml). The cell medium was aspirated at the time designated and cell lysates were subjected to immunoblotting applying anti-heparanase antibody (upper and third panels). Note an almost complete inhibition of heparanase uptake by mAb 9E8. Heparanase-transfected 293 cells were grown with control mouse IgM or mAb 9E8 for two days. Cells were then fixed with methanol and subjected to immunofluorescent staining applying anti heparanase antibody (second panel) or lysed and subjected to immunoblotting applying anti-heparanase antibody (fourth panel). Purified recombinant active heparanase (200 ng) was pre-incubated with control mouse IgM (♦), mAb 8A5 (※), mAb 9E8 ( ※ ), all at 2 µg/ml, for 2 h in serum-free RPMI medium on ice. The mixture was then applied onto $^{35}$S-labeled ECM-coated dishes and heparanase activity was determined as described above (lower panel). FIG. 3B, C. ESb mouse T-lymphoma cells (5×10$^5$) were inoculated subcutaneously in NOD/SCID mice (n=5) and treated with PG545 (20 mg/kg, once a week) (B) or the indicated mAb (500 µg/mouse every other day) (C). Survival of mice treated with PG545 vs. vehicle (Con) is presented in FIG. 3B. FIG. 3C. Livers of mice treated with mAb 9E8 were removed after 3 weeks; photographed (upper panels), and five micron sections of formalin-fixed, paraffin-embedded liver tissue were subjected to immunostaining applying anti-CD45 antibody (second panels). Quantification of the extent of CD45 staining is shown graphically in the lower panel. Original Magnifications: upper panel x1; second panel x20.

Example 4

Inhibition of Lymphoma Tumor Progression and Bone Colonization by Heparanase-Neutralizing Monoclonal Antibodies 9E8

Figures 4A, 4B:
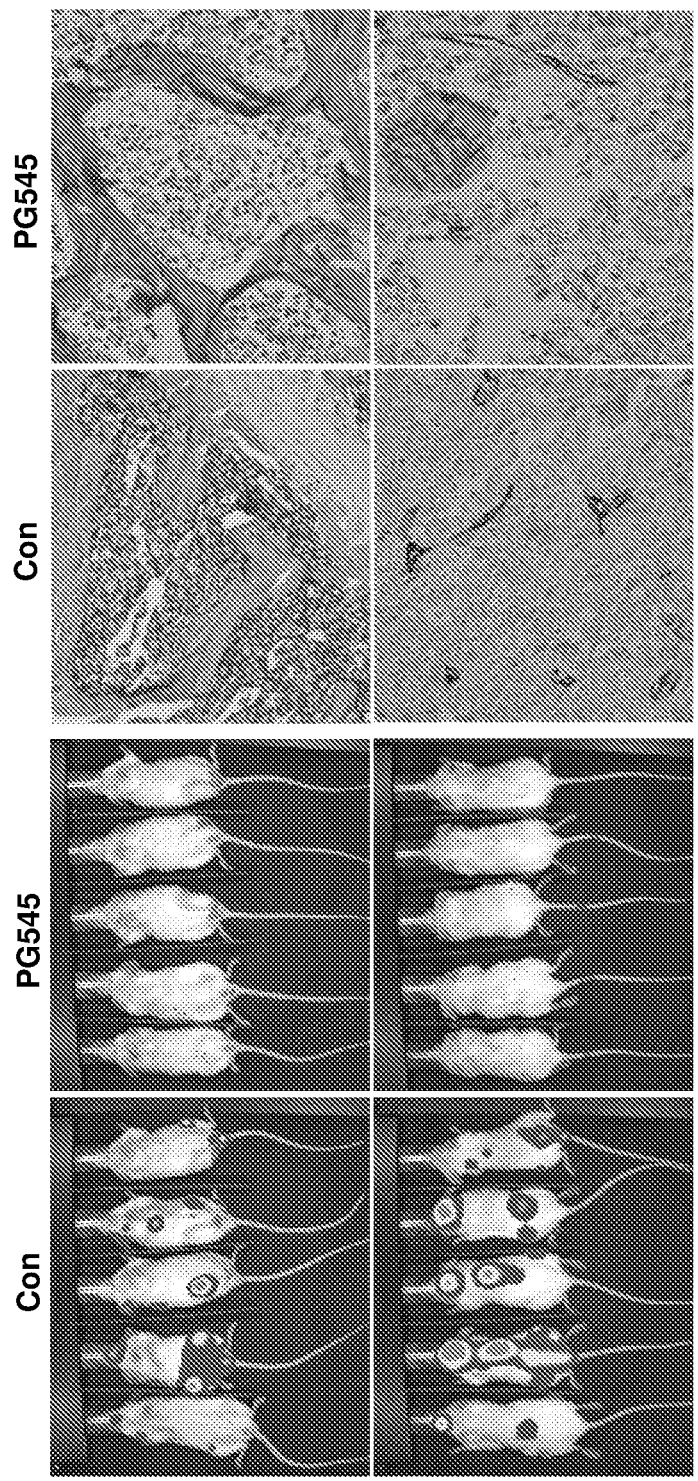
FIG. 4A shows photos of mice inoculated (intravenously) with Raji-luciferase lymphoma cells and treated with compound PG545. It also shows the inhibitory effect of PG545 on vessel density and homing of the lymphoma cells to the bone marrow.
FIG. 4B shows photos of Raji cells in the bone marrow of mice untreated (con) or treated with PG545 (upper panels). Same tissue sections were similarly stained with anti-CD31 antibody that marks blood vessels (lower panels).
Figure 4C:
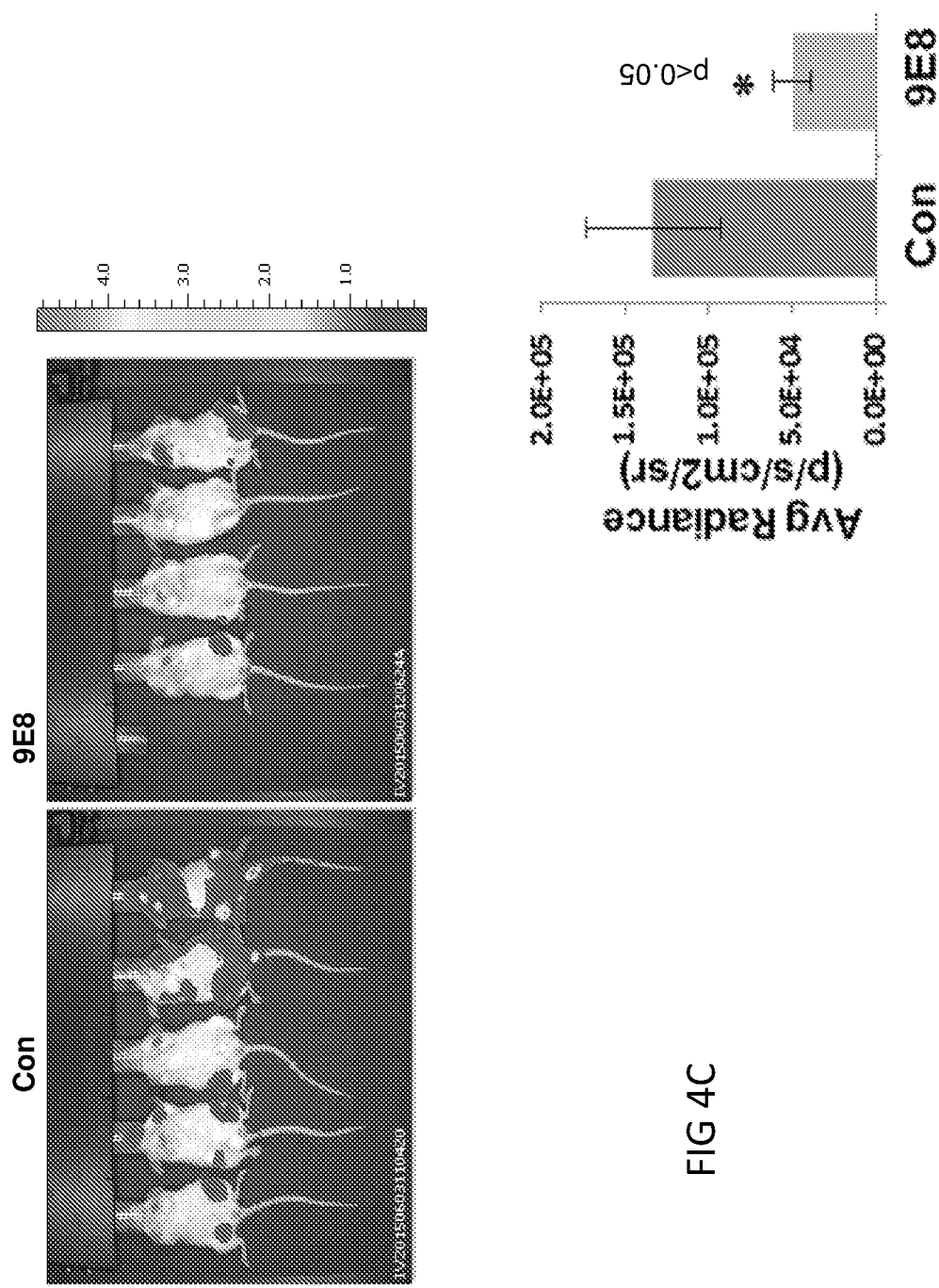
FIG. 4C shows photos of mice inoculated (intravenously) with Raji-luciferase lymphoma cells and treated with mAb 9E8. Quantification of luciferase signals is shown graphically in the right lower panel.

The ability of neutralizing mAbs 9E8 to restrain tumor growth, applying luciferase-labelled cells and IVIS bioluminescent imaging that enables accurate quantification of tumor load was then examined. Homing and expansion in the bone marrow was observed following inoculation of Raji-luciferase cells into the tail vein of NOD/SCID (FIG. 4A, Con), expansion that was markedly reduced by PG545 (FIG. 4A, B, PG) associating with decreased blood vessel density (FIG. 4B, lower panels). Most importantly, Raji cell growth was decreased 2-3 fold by mAbs 9E8 (FIG. 4C)

These results strongly indicate that lymphoma growth can be restrained by specific neutralization of heparanase enzymatic activity within the tumor microenvironment (Weissmann et al, 2016, Proc Natl Acad Sci USA 113:704-709).
Detailed Description of FIGS. 4A-4C FIG. 4A. Raji-luciferase cells ($1 \times 10^6$) were injected into the tail vein of NOD/SCID mice (n=5). Mice were treated with PG545 (20 mg/kg once a week) starting one day after cell inoculation and IVIS imaging was applied to quantify tumor load. Homing of Raji cells to the bone marrow was further confirmed by immunostaining of decalcified backbone sections with anti-human HLA that labels human cells (FIG. 4B, upper panels). Slides were similarly stained with anti-CD31 antibody that marks blood vessels (FIG. 4B, lower panels). FIG. 4C. NOD/SCID mice (n=5) were inoculated (iv) with Raji-luciferase cells and mice were treated with mAb 9E8 (600 µg/mouse every other day) (FIG. 4C) and tumor growth was evaluated by IVIS imaging (left panels). Quantification of luciferase signals is shown graphically in the right lower panel.

Example 5

Heparanase Neutralizing mAbs (9E8) Attenuate Cell Invasion and Tumor Metastasis

As was explained in Example 3, mAb 9E8 neutralizes heparanase enzymatic activity to magnitude comparable with the polyclonal antibody #1453 (and inhibits cell invasion and tumor metastasis, the hallmarks of heparanase activity (FIG. 5A-C).
Detailed Description of FIGS. 5A-5C FIG. 5A. Cell invasion. Cal-27 tongue carcinoma (left panels) and U87 glioma cells (right panels) ($2 \times 10^5$) were plated onto Matrigel-coated filters in the presence of mouse IgM/IgG (upper panels), mAb 9E8 (2 µg; second left and middle panels). Invading cells adhering to the lower side of the membrane were visualized after 6 h. The number of invading cells per high power field is shown graphically at the lower panels. FIG. 5B, FIG. 5C. Tumor metastasis. FIG. 5B Mouse B16 melanoma cells ($2 \times 10^5$) were inoculated into the tail vein of C57Bl/6 mice (n=7) together with rabbit IgG (300 µg; Con), Ab #1453 (250 µg), mAb 9E8 (500 µg) or SST0001 (400 µg). Lungs were harvested after 18 days, photographed (lower panel) and the number of metastatic lesions was counted (upper panel; p=0.001, 0.0006, 0.0001 for Con vs. Ab 1453, Con vs. mAb 9E8 and Con vs. SST0001, respectively). FIG. 5C LM2-4 human breast carcinoma cells ($2 \times 10^6$) were inoculated into the tail vein of NOD/SCID mice (n=5) together with PBS or mAb 9E8 (500 µg/mouse). Lungs were harvested after 18 days and photographed (FIG. 5C, right panels). The respective lung tissue sections are presented (FIG. 5C, left panels).

Example 6

Figure 6A:
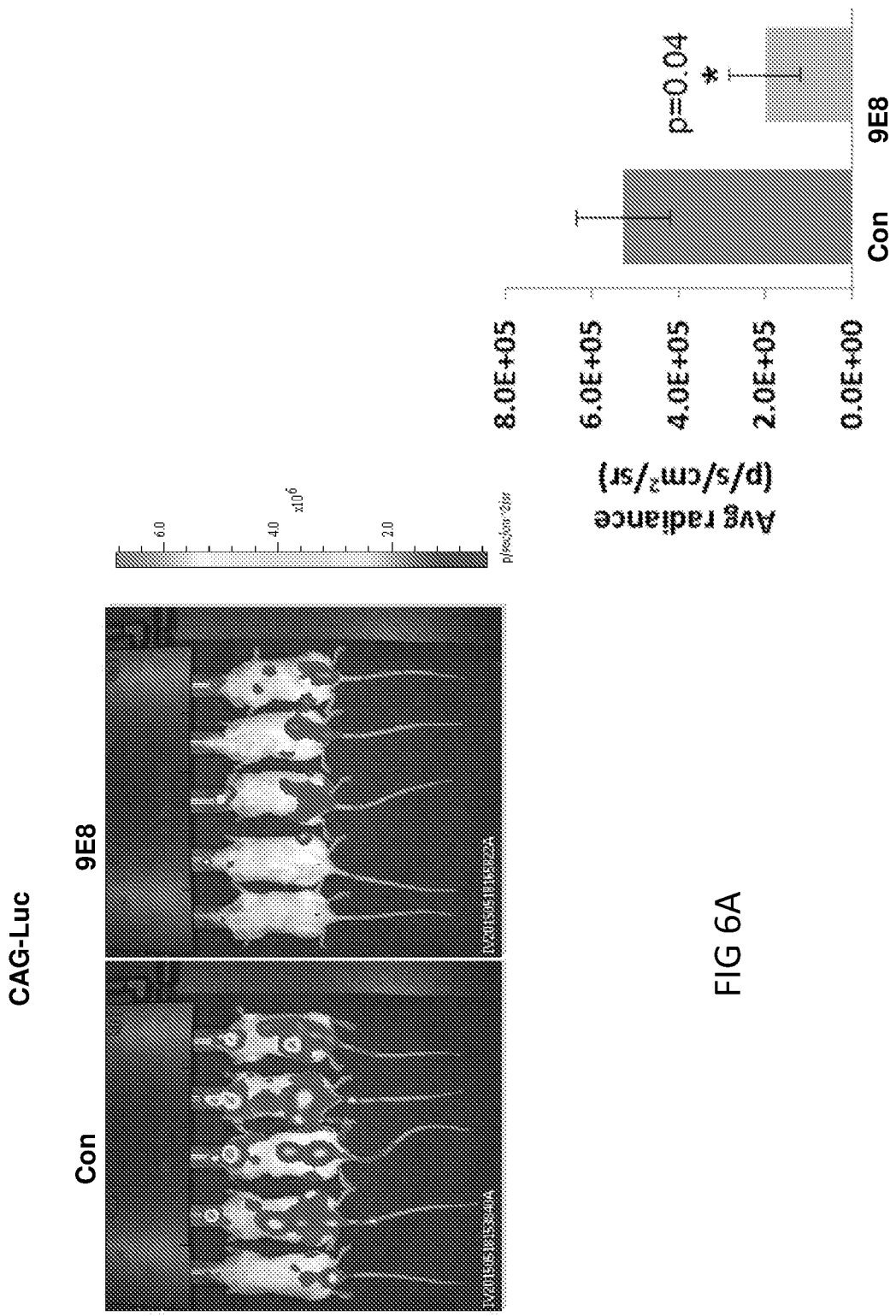
FIG. 6A (right and left panels) shows photos of mice inoculated (intravenously) with CAG-luciferase human myeloma cells and treated with mAb 9E8 as single agent. Same is shown graphically at the lower left panels.
Figure 6B:
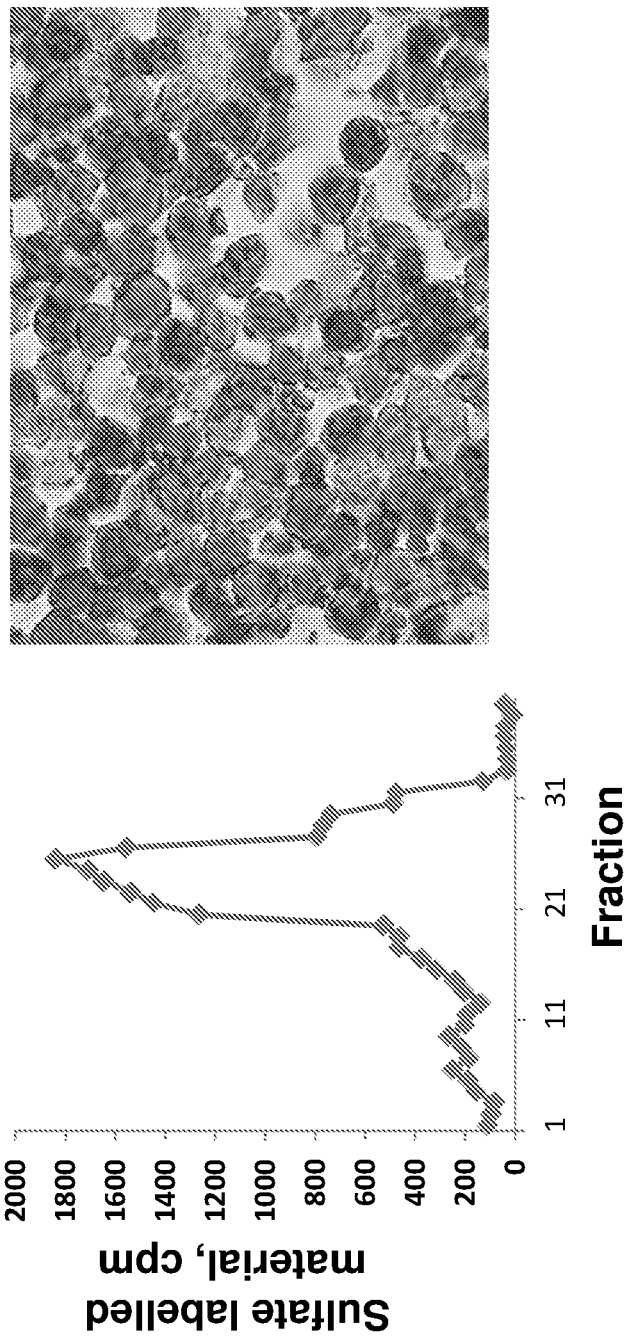
FIG. 6B shows line graph (left panel) and histological (right panel) specimen showing heparanase immunostaining and enzymatic activity in the bone marrow of mice inoculated with CAG myeloma cells.
Figure 6C:
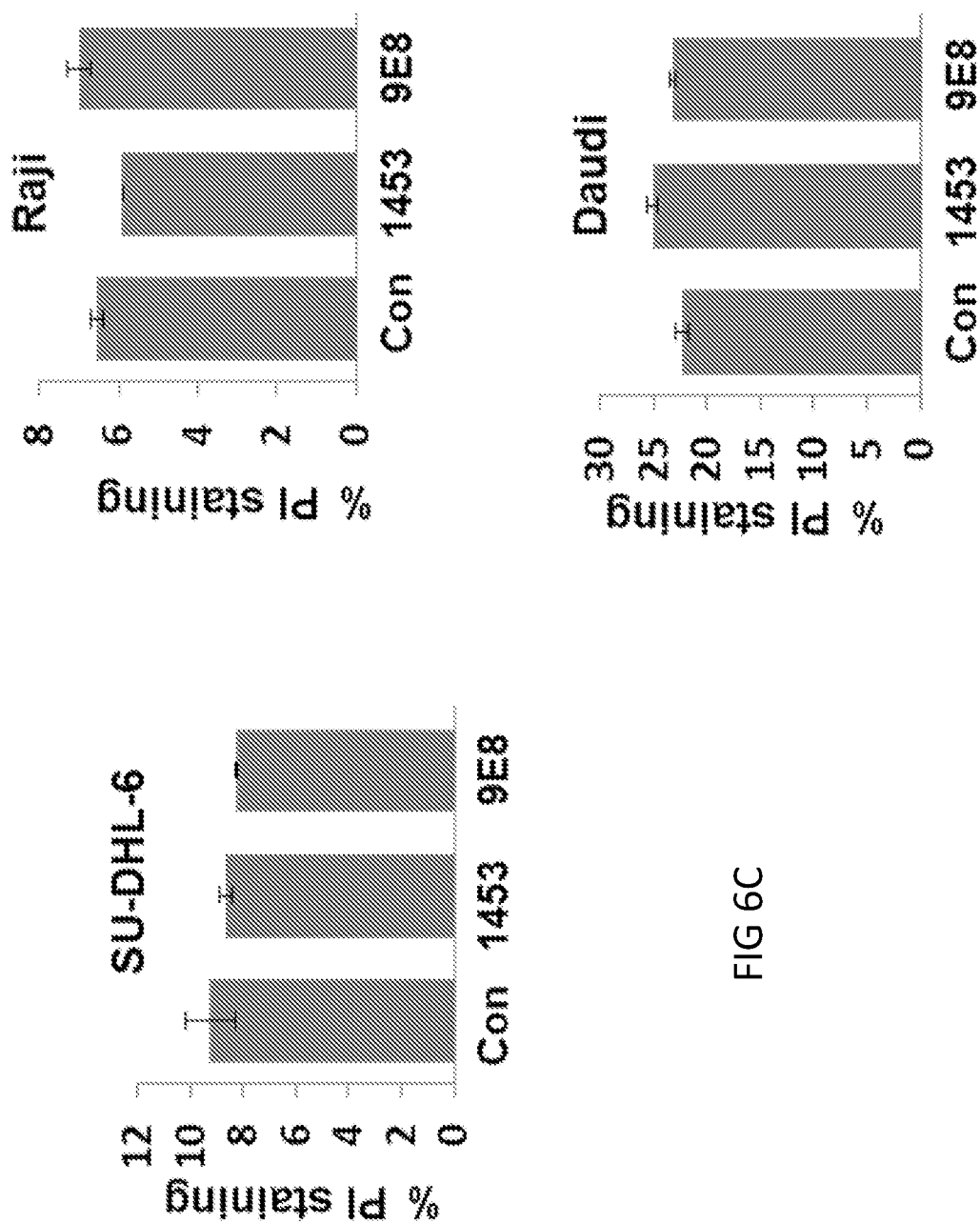
FIG. 6C shows bar graphs showing that the neutralizing anti-heparanase antibodies do not elicit lymphoma cell death.

Heparanase-Neutralizing mAb (9E8) Restrain Myeloma Tumor Growth and Dissemination To this end, CAG myeloma cells shown previously to strictly depend on heparanase activity for tumor expansion (Ritchie J P, et al. 2011, SST0001, Clin Cancer Res 17(6): 1382-1393) were used. Following tail vein inoculation, CAG-luciferase cells home to and expand in the bone marrow (FIG. 6A, Con). The bone marrow exhibits high heparanase activity (FIG. 6B, left) and a high percentage of heparanase-positive cells (FIG. 6B, right) and thus appears as a supportive environment that can be targeted by the neutralizing mAbs. Notably, IVIS imaging and analysis revealed a significant, 2-3 fold decrease in tumor burden following treatment with mAb 9E8 (FIG. 6A).
Detailed Description of FIGS. 6A-6C FIG. 6A. CAG myeloma. NOD/SCID mice (n=5) were inoculated (iv) with CAG-luciferase cells ($5 \times 10^6$) and mice were treated with mAb 9E8 (600 µg/mouse every other day). Tumor growth was evaluated by IVIS imaging (left panels). Quantification of luciferase signals is shown graphically in the right panel. Note 2-3 fold decrease in tumor growth by the heparanase-neutralizing mAbs. FIG. 6B. Bone marrow was harvested from C57Bl/6 mice, cells were collected by centrifugation and heparanase activity was determined as described under 'Materials and Methods' (left panel). Corresponding bones were fixed in formalin and following de-calcification were subjected to immunostaining applying anti-heparanase antibody (right panel). FIG. 6C. The indicated cell line ($0.25 \times 10^6$) was treated with antibodies 1453or 9E8 (50 µg/ml) for 24 h. Cells were then washed once with FACS buffer (PBS containing 2% FCS), incubated with Propidium Iodide (PI; 1 µg/ml) for 10 min and analyzed using FACS Cyan ADP system (Beckman Coulter, Inc). PI-positivity indicates a disturbed membrane and cell death. Note that anti-heparanase antibodies do not elicit lymphoma cell death.

Example 7

Effect of 9E8-IgG Clones (IgM to IgG Conversion) on Heparanase Activity

Class switch of monoclonal 9E8 IgM antibodies to IgG. A "cloning free" approach to generate antibodies with altered heavy chain isotype by mimicking the germinal center reaction in antibody-secreting hybridoma cells. This was accomplished by electroporation and controllable expression of activation-induced cytidine deaminase (AID) to generate immunoglobulin somatic hypermutation (SHM) and class switch recombination (CSR) in antibody genes (Su Y C et al., 2014, MAbs 6:1069-83). This was further coupled with high-throughput fluorescence-activated cell sorting (FACS) of hybridoma cells to generate class switched heavy chain variants of monoclonal IgM to monoclonal IgG. The method enables rapid class switch of monoclonal IgM antibodies to IgG directly in hybridoma cells with the caveat that simultaneous SHM may also improve antibody binding properties (Su Y C et al., 2014, MAbs 6:1069-83).

Figure 7A:
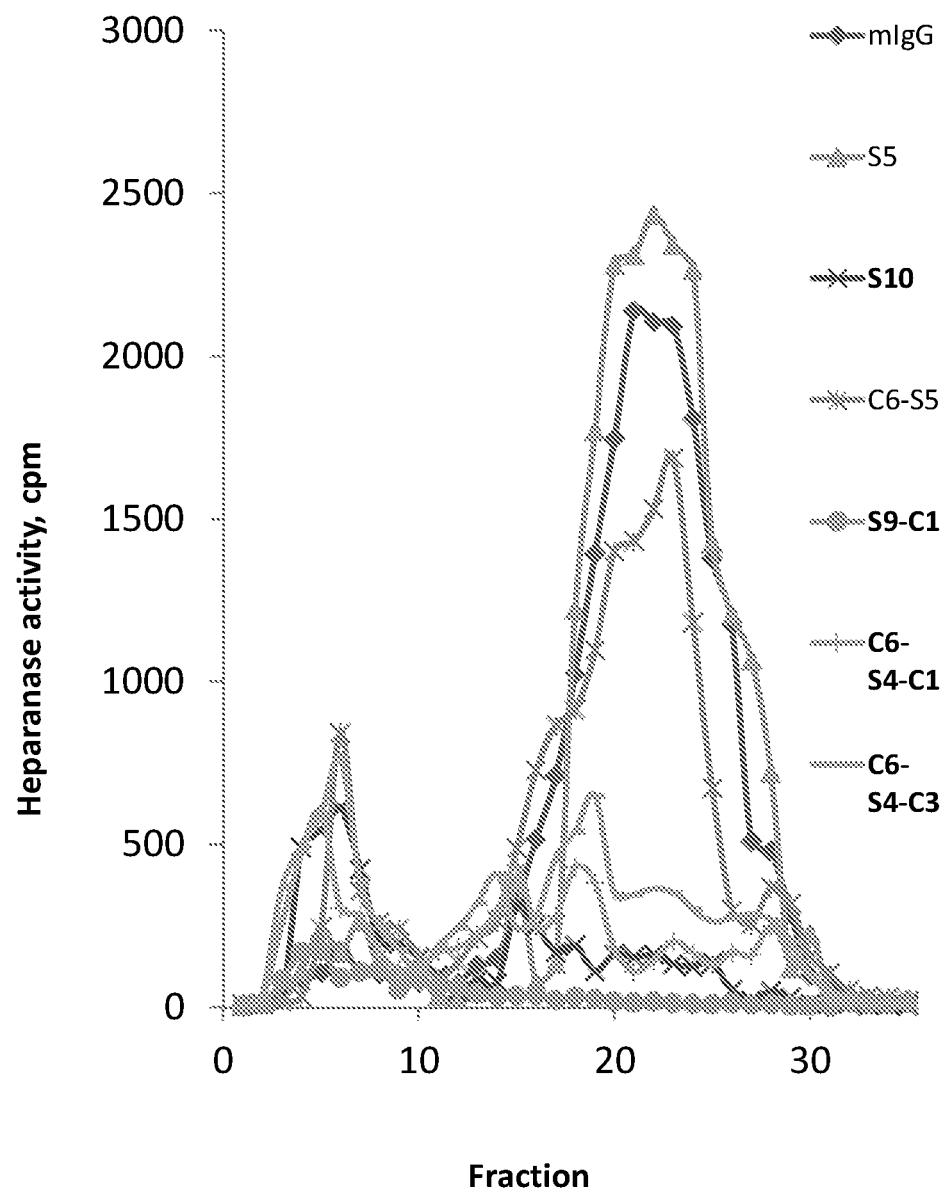
FIG. 7 shows line graphs representing the effect of 9E8 clones converted from IgM to IgG on the enzymatic activity of recombinant heparanase. Clones S9-C1 and C6-S4-C3 markedly inhibited heparanase activity.
Figure 8:
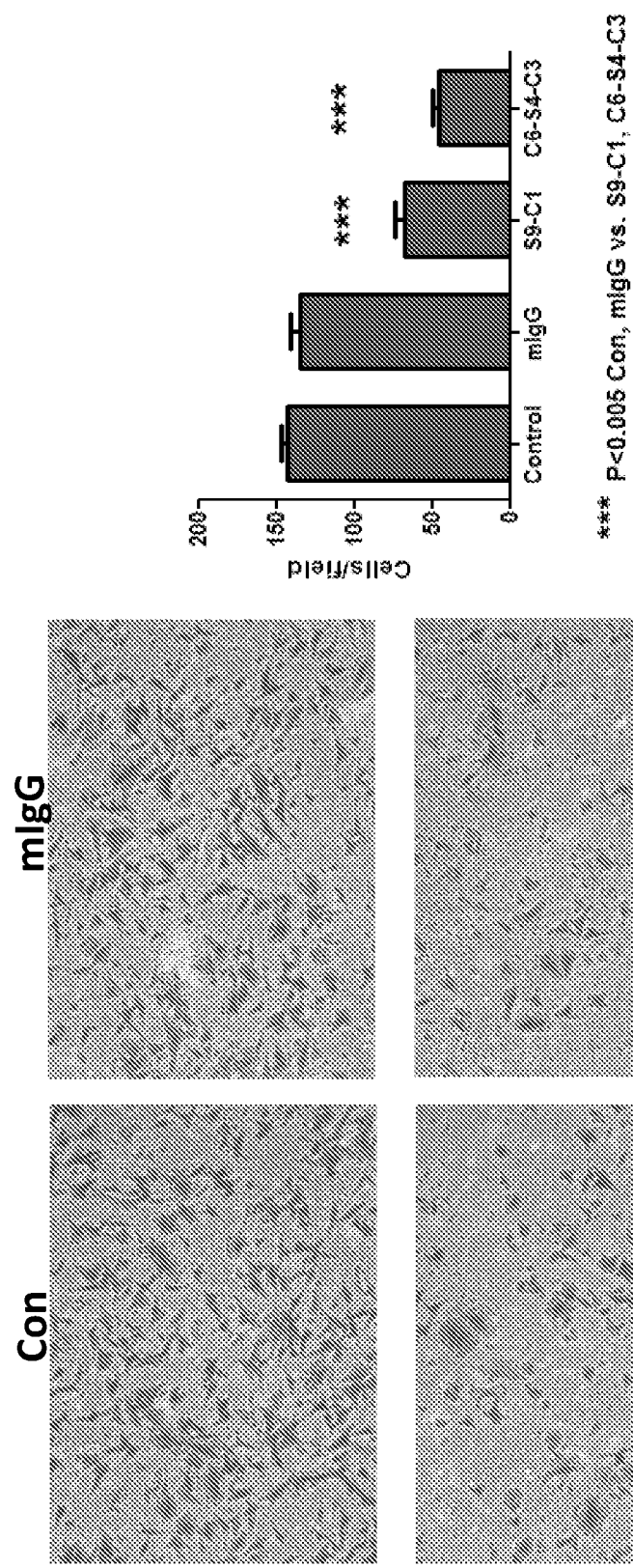
FIG. 8 shows photomicrographs (left panel) and bar graphs (right panel) representing the effect of 9E8-IgG clones on U87 glioma cell invasion. Clones S9-C1 and C6-S4-C3 markedly inhibited cell invasion (bars).

Briefly, our hybridoma cells producing the 9E8 IgM antibodies were stably transfected (electroporation) with a construct encoding for AID and GFP reporter (and containing Lox-Cre recombination sites to allow removal of the AID-GFP upon obtaining the desirable clones), followed by selection (puromycin) and cell expansion to allow SHM and CSR of immunoglobulin genes. This was followed by multiple rounds of selection with biotin-labeled heparanase (detected by fluorescent streptavidin) and sorting (FACS) for surface IgG expressing cells that bind heparanase. This procedure yielded hybridoma that secretes affinity maturated anti-heparanase antibodies that were classified as IgG1.

i) Heparanase neutralization by mAb 9E8-IgG. Several clones were selected, expanded and tested for neutralization of heparanase enzymatic activity applying sulfate labeled ECM as substrate (Vlodaysky I, et al. 1999, Nature Med 5(7):793-802). Briefly, this method measures the release of heparan sulfate degradation fragments from a naturally produced ECM coating the surface of 35 mm culture dishes (Vlodaysky I, et al. 1999, Nature Med 5(7):793-802). Mouse IgG (mIgG) served as a negative control. At 40 µg/ml, heparanase activity was completely blocked in the presence of clone S9-C1 (FIG. 7A), while clones C6-S4-C1, C6-S4-C3 and S10 yielded a nearly complete inhibition (FIG. 7A). Clone C9-C1 yielded partial (~80%) inhibition at lower (10 and 20 µg/ml) concentrations (FIG. 7B).

ii) Inhibition of tumor cell invasion by mAb 9E8-IgG. The most effective heparanase neutralizing IgG mAbs were tested for inhibition of U87 glioma cell invasion through a reconstituted basement membrane-like substrate (Matrigel). Clones S9-C1 and C6-S4-C3 yielded statistically significant (p<0.005) 50% and 70% inhibition of cell invasion (FIG. 8).

Figure 7B:
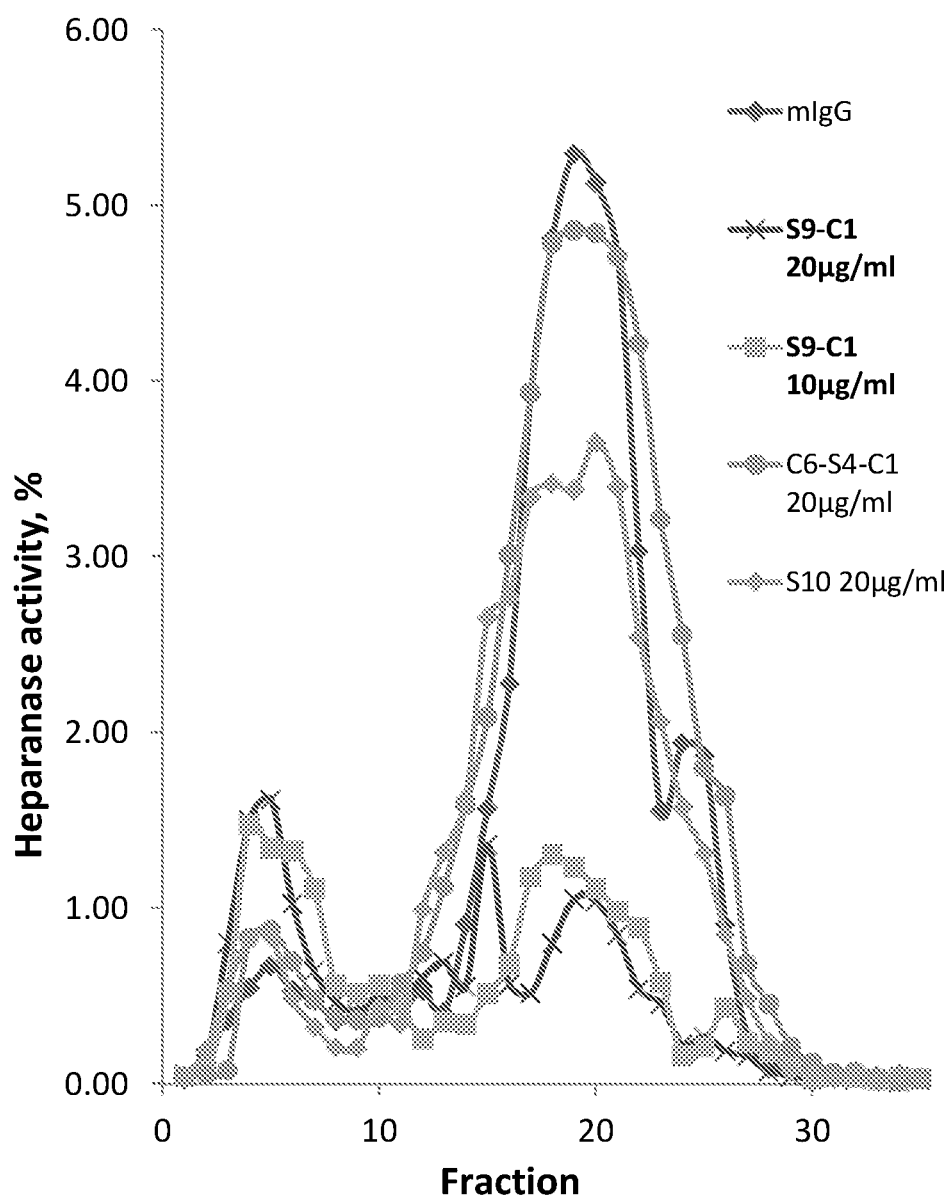

Detailed Description of FIGS. 7A and 7B

FIGS. 7A and B. Purified recombinant active heparanase (200 ng) was pre-incubated with control mouse IgG, and each of the 9E8-IgG clones, all at 40 µg/ml (FIG. 7A) or 10 and 20 µg/ml (FIG. 7B), for 2 h in serum-free RPMI medium on ice. The mixture was then incubated (12 h, 37° C., pH 6.0) with $^{35}$S-labeled ECM-coated dishes. Sulfate labeled degradation fragments released into the incubation medium were analyzed by gel filtration on a Sepharose CL-6B column. Degradation fragments of HS side chains are eluted from Sepharose 6B at 0.5<Kav<0.8 (peak II, fractions 17-30). Clones S9-C1, C6-S4-C1, C6-S4-C3 and S10 inhibited the enzyme.

Example 8

Effect of 9E8-IgG Clones on Tumor Cell Invasion

U87 glioma cells ($2\times10^5$) were plated onto Matrigel-coated 8 micron transwell filters in the absence (Con) or presence of mouse IgG (mIgG), or the 9E8-IgG heparanase neutralizing clones S9-C1 and C6-S4-C3. Following 6 h incubation, invading cells adhering to the lower side of the membrane were fixed, stained with 0.5% crystal violet, photographed and counted by examination of at least seven microscopic fields (bars). Clones S9-C1 and C6-S4-C3 markedly inhibited cell invasion (p<0.005, bars), as can be clearly seen from FIG. 8

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An isolated monoclonal antibody (mAb) directed to the Lys158-Asp171 domain of human heparanase, wherein the mAb comprises a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO: 6.

2. The mAb of claim 1, comprising a heavy chain variable domain having a sequence set forth in SEQ ID NO: 7 and a light chain variable domain having a sequence set forth in SEQ ID NO: 8.

3. The mAb of claim 1, wherein the antibody is attached to a functional moiety.

4. The mAb of claim 3, wherein the functional moiety is a marker, detectable tag, cytotoxic molecule or therapeutic agent.

5. The mAb of claim 1, wherein the monoclonal antibody is of an immunoglobulin class including IgG, IgM, IgE, or IgA.

6. The mAb of claim 5, wherein said IgA is IgA1 or IgA2 said IgG is IgG1, IgG2, IgG3, or IgG4.

7. The mAb of claim 1, wherein the heavy chain variable domain is joined to the constant heavy region of a human IgG antibody subtype.

8. The mAb of claim 1, wherein the mAb has a heparanase neutralizing effect.

9. The mAb of claim 1, wherein the Lys158-Asp171 domain of human heparanase has the amino acid sequence set forth in SEQ ID NO: 11.

10. A pharmaceutical composition comprising the mAb of claim 1 and a pharmaceutically acceptable carrier.

11. A method for treating lymphoma in a subject in need thereof, comprising administering to the subject a therapeutically effective amount of the mAb of claim 1, thereby treating the lymphoma in said subject.

12. The method of claim 11, wherein the lymphoma is a B-cell lymphoma.

13. The method of claim 12, wherein the B-cell lymphoma is selected from the group consisting of Burkitt lymphoma, Hodgkin's lymphoma, non-Hodgkin's lymphoma, follicular lymphoma, small lymphocytic lymphoma, diffuse B-cell lymphoma, mantle cell lymphoma, and marginal zone lymphoma.

14. A method for treating multiple myeloma in a subject in need thereof, comprising administering to the subject a therapeutically effective amount of the mAb of claim 1.

15. The method of claim 10, wherein said mAb is administered in combination with an anti-cancer treatment.

* * * * *